(12) United States Patent
Karst et al.

(10) Patent No.: US 8,996,109 B2
(45) Date of Patent: Mar. 31, 2015

(54) LEADLESS INTRA-CARDIAC MEDICAL DEVICE WITH DUAL CHAMBER SENSING THROUGH ELECTRICAL AND/OR MECHANICAL SENSING

(75) Inventors: Edward Karst, South Pasadena, CA (US); Richard Samade, Northridge, CA (US); Gene A. Bornzin, Simi Valley, CA (US); John W. Poore, South Pasadena, CA (US); Zoltan Somogyi, Simi Valley, CA (US); Didier Theret, Porter Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 224 days.

(21) Appl. No.: 13/485,513

(22) Filed: May 31, 2012

(65) Prior Publication Data
US 2013/0325081 A1    Dec. 5, 2013

(51) Int. Cl.
| *A61N 1/00* | (2006.01) |
| *A61N 1/365* | (2006.01) |
| *A61N 1/375* | (2006.01) |
| *A61N 1/372* | (2006.01) |
| *A61B 5/00* | (2006.01) |
| *A61B 5/042* | (2006.01) |

(Continued)

(52) U.S. Cl.
CPC .......... *A61N 1/36592* (2013.01); *A61N 1/3756* (2013.01); *A61B 5/0452* (2013.01); *A61N 1/36507* (2013.01); *A61N 1/36514* (2013.01); *A61N 1/368* (2013.01); *A61N 1/37205* (2013.01); *A61N 1/36578* (2013.01); *A61B 5/6869* (2013.01); *A61B 5/6882* (2013.01); *A61B 5/0422* (2013.01); *A61B 5/0464* (2013.01); *A61B 5/1107* (2013.01); *A61B 2560/0468* (2013.01)
USPC ......................................................... 607/25

(58) Field of Classification Search
CPC ..................................................... A61N 1/3627
USPC .......................................................... 607/25
See application file for complete search history.

(56) References Cited

U.S. PATENT DOCUMENTS

| 3,835,864 A | 9/1974 | Rasor et al. |
| 3,835,869 A | 9/1974 | Newman et al. |

(Continued)

FOREIGN PATENT DOCUMENTS

| EP | 1844812 A1 | 10/2007 |
| WO | 2005092431 A1 | 10/2005 |

(Continued)

OTHER PUBLICATIONS

Asirvatham, Samuel J. MD et al., "Intramyocardial Pacing and Sensing for the Enhancement of Cardiac Stimulation and Sensing Specificity," Pace. 2007;30:748-754.

(Continued)

*Primary Examiner* — Christopher D Koharski
*Assistant Examiner* — Nadia A Mahmood
(74) *Attorney, Agent, or Firm* — Theresa A. Raymer

(57) ABSTRACT

A leadless intra-cardiac medical device senses cardiac activity from multiple chambers and applies cardiac stimulation to at least one cardiac chamber and/or generates a cardiac diagnostic indication. The leadless device may be implanted in a local cardiac chamber (e.g., the right ventricle) and detect near-field signals from that chamber as well as far-field signals from an adjacent chamber (e.g., the right atrium).

33 Claims, 10 Drawing Sheets

(51) Int. Cl.
*A61B 5/11* (2006.01)
*A61B 5/0452* (2006.01)
*A61N 1/368* (2006.01)
*A61B 5/0464* (2006.01)

(56) References Cited

U.S. PATENT DOCUMENTS

| | | | |
|---|---|---|---|
| 3,943,936 | A | 3/1976 | Rasor et al. |
| 4,987,897 | A | 1/1991 | Funke |
| 5,193,540 | A | 3/1993 | Schulman et al. |
| 5,358,514 | A | 10/1994 | Schulman et al. |
| 5,405,367 | A | 4/1995 | Schulman et al. |
| 5,411,535 | A | 5/1995 | Fujii et al. |
| 5,487,758 | A | 1/1996 | Hoegnelid et al. |
| 5,545,201 | A | 8/1996 | Helland et al. |
| 5,679,022 | A | 10/1997 | Cappa et al. |
| 5,814,089 | A | 9/1998 | Stokes et al. |
| 6,141,588 | A | 10/2000 | Cox et al. |
| 6,164,284 | A | 12/2000 | Schulman et al. |
| 6,181,965 | B1 | 1/2001 | Loeb et al. |
| 6,185,452 | B1 | 2/2001 | Schulman et al. |
| 6,208,894 | B1 | 3/2001 | Schulman et al. |
| 6,434,428 | B1 | 8/2002 | Sloman et al. |
| 6,754,536 | B2 | 6/2004 | Swoyer et al. |
| 7,047,076 | B1 | 5/2006 | Li et al. |
| 7,082,336 | B2 | 7/2006 | Ransbury et al. |
| 7,114,502 | B2 | 10/2006 | Schulman et al. |
| 7,363,087 | B2 | 4/2008 | Nghiem et al. |
| 7,383,091 | B1 * | 6/2008 | Chitre et al. ............ 607/127 |
| 7,513,257 | B2 | 4/2009 | Schulman et al. |
| 7,565,195 | B1 | 7/2009 | Kroll et al. |
| 7,630,767 | B1 | 12/2009 | Poore et al. |
| 7,634,313 | B1 | 12/2009 | Kroll et al. |
| 7,643,872 | B2 | 1/2010 | Min et al. |
| 7,801,626 | B2 | 9/2010 | Moser |
| 7,860,570 | B2 | 12/2010 | Whitehurst et al. |
| 7,894,915 | B1 | 2/2011 | Chitre et al. |
| 7,899,555 | B2 | 3/2011 | Morgan et al. |
| 7,937,148 | B2 | 5/2011 | Jacobson |
| 7,945,333 | B2 | 5/2011 | Jacobson |
| 8,010,209 | B2 | 8/2011 | Jacobson |
| 8,032,219 | B2 | 10/2011 | Neumann et al. |
| 2004/0015204 | A1 | 1/2004 | Whitehurst et al. |
| 2004/0015205 | A1 | 1/2004 | Whitehurst et al. |
| 2004/0147973 | A1 | 7/2004 | Hauser |
| 2006/0009831 | A1 | 1/2006 | Lau et al. |
| 2006/0135999 | A1 | 6/2006 | Bodner et al. |
| 2006/0136004 | A1 | 6/2006 | Cowan et al. |
| 2007/0055310 | A1 | 3/2007 | Lau |
| 2007/0078490 | A1 | 4/2007 | Cowan et al. |
| 2007/0088396 | A1 | 4/2007 | Jacobson |
| 2007/0088400 | A1 | 4/2007 | Jacobson |
| 2007/0156056 | A1 * | 7/2007 | Min et al. ............ 600/509 |
| 2008/0097566 | A1 | 4/2008 | Colliou |
| 2008/0255647 | A1 | 10/2008 | Jensen et al. |
| 2009/0082828 | A1 | 3/2009 | Ostroff |
| 2009/0299433 | A1 | 12/2009 | Dingman et al. |
| 2010/0010381 | A1 | 1/2010 | Skelton et al. |
| 2010/0198288 | A1 | 8/2010 | Ostroff |
| 2010/0228308 | A1 | 9/2010 | Cowan et al. |
| 2011/0071586 | A1 | 3/2011 | Jacobson |
| 2011/0077708 | A1 | 3/2011 | Ostroff |
| 2011/0208260 | A1 | 8/2011 | Jacobson |
| 2011/0218587 | A1 | 9/2011 | Jacobson |
| 2011/0238077 | A1 | 9/2011 | Wenger |
| 2011/0251660 | A1 | 10/2011 | Griswold |
| 2011/0251662 | A1 | 10/2011 | Griswold et al. |

FOREIGN PATENT DOCUMENTS

| | | |
|---|---|---|
| WO | 2007047681 A2 | 4/2007 |
| WO | 2008039619 A2 | 4/2008 |
| WO | 2007047681 A3 | 9/2008 |
| WO | 2009039400 A1 | 3/2009 |
| WO | 2009078751 A1 | 6/2009 |
| WO | 2010088687 A1 | 8/2010 |

OTHER PUBLICATIONS

Brinker, Jeffrey A., "Endocardial Pacing Leads: The Good, the Bad, and the Ugly," Pace. 1995;18(Pt 1):953-954.

Calvagna, Giuseppe M. et al., "A complication of pacemaker lead extraction: pulmonary embolization of an electrode fragment," Europace. 2010;12:613.

Da Costa, Sergio Sidney Do Carmo et al., "Incidence and Risk Factors of Upper Extremity Deep Vein Lesions After Permanent Transvenous Pacemaker Implant: A 6-Month Follow-up Prospective Study," Pace. 2002;25:1301-1306.

Hauser, Robert G. et al., "Deaths and cardiovascular injuries due to device-assisted implantable cardioverter-defibrillator and pacemaker lead extraction," Europace. 2010;12:395-401.

Heaven, D.J. et al., "Pacemaker lead related tricuspid stenosis: a report of two cases," Heart. 2000;83:351-352.

Henz, Benhur D. MD et al., "Synchronous Ventricular Pacing without Crossing thetricuspid Valve or Entering the Coronary Sinus—Preliminary Results," J Cardiovasc Electrophysiol. (Dec. 2009);20:1391-1397.

Hesselson, Aaron B. Bsee et al., "Deleterious Effects of Long-Term Single-chamber Ventricular Pacing in Patients With Sick Sinus Syndrome: The Hidden Benefits of dual-Chamber Pacing," J Am Coll Cardiol. 1992;19:1542-1549.

Klug, Didier MD et al., "Systemic Infection Related to Endocardities on Pacemaker Leads—Clinical Presentation and Management," Circulation. 1997;95:2098-2107.

Korkeila, Petri et al., "Clinical and laboratory risk factors of thrombotic complications after pacemaker implantation: a prospective study," Europace. 2010;12:817-824.

Marrie, Thomas J. MD et al., "A Scanning and Transmission Electron Microscopic Study of an Infected Endocardial Pacmaker Lead," Circulation. 1982;66(6):1339-1341.

Menozzi, Carlo et al., "Intrapatient Comparison Between Chronic VVIR and DDD pacing in Patients Affected by High Degree AV Block Without Heart Failure," Pace. (Dec. 1990—Pt II);13:1816-1822.

Stellbrink, Christoph et al.,"Technical considerations in implanting left ventricular pacing leads for cardiac resynchronization therapy," European Heart Journal Supplements. 2004;6(Supp D):D43-D46.

Stickler, J. William PhD, "Totally Self-Contained Intracardiac Pacemaker," J Electrocardiology. 1970;3(3-4):325-331.

Van Rooden, Cornelis J. MD et al., "Incidence and Risk Factors of Early Venous Thrombosis Associated with Permanent Pacemaker Leads," J Cardiovasc Electrophysiol. (Nov. 2004);15:1258-1262.

Vardas, P.E. et al., "A Miniature Pacemaker Introduced Intravenously and Implanted Endocardially. Preliminary Findings from an Experimental Study," Eur J Card Pacing Electrophysiol. 1991;1:27-30.

Voet, J.G. et al., "Pacemaker lead infection: report of three cases and review of the literature," Heart. 1999;81:88-91.

Walters, M.I. et al., "Pulmonary Embolization of a Pacing Electrode Fragment Complicating Lead Extraction," Pace. 1999;22:823-824.

* cited by examiner

LEADLESS INTRA-CARDIAC MEDICAL DEVICE WITH DUAL CHAMBER SENSING THROUGH ELECTRICAL AND/OR MECHANICAL SENSING

CROSS REFERENCE TO RELATED APPLICATIONS

This application relates to U.S. patent application Ser. No. 13/352,048, filed Jan. 17, 2012, entitled "Single-Chamber Leadless Intra-Cardiac Medical Device with Dual-Chamber Functionality" (now U.S. Pat. No. 8,798,740); Ser. No. 13/352,136, filed Jan. 17, 2012, entitled "Dual-Chamber Leadless Intra-Cardiac Medical Device with Intra-Cardiac Extension" (now U.S. Pat. No. 8,634,912); and Ser. No. 13/485,534, filed May 31, 2012, entitled "Single Chamber Leadless Intra-Cardiac Medical Device Having Dual Chamber Sensing with Signal Discrimination", (now U.S. Patent Publication No. 2013/0138006), which are hereby incorporated by reference in their entirety.

FIELD OF THE INVENTION

Embodiments of the present invention generally relate to leadless implantable medical devices, and more particularly to leadless intra-cardiac medical devices that afford dual chamber sensing from a position within a single chamber of the heart through electrical and/or electro-mechanical means. As used herein, the term "leadless" generally refers to an absence of electrically-conductive leads that traverse vessels or other anatomy outside of the intra-cardiac space, while "intra-cardiac" means generally, entirely within the heart and associated vessels, such as the SVC, IVC, CS, pulmonary arteries and the like.

BACKGROUND OF THE INVENTION

An implantable device, such as an implantable cardiac rhythm management device (e.g., a pacemaker, a defibrillator, or a cardioverter), may be used to monitor cardiac function and provide therapy for a patient who suffers from cardiac arrhythmia. For example, in an attempt to maintain regular cardiac rhythm, the implantable device may track the type and timing of native cardiac signals. In this way, the implantable device may determine whether cardiac events (e.g., contractions) are occurring and whether they are occurring at the proper times.

The implantable device may track cardiac signals through the use of one or more leads implanted in or near the heart of the patient. For example, the implantable device may process signals received via implanted leads and then attempt to characterize the received signals as a particular cardiac event. Such cardiac events may include, for example, P waves, R waves, T waves, or arrhythmia events. By analyzing the type and timing of these cardiac events, the implantable device may determine whether therapy should be provided and, if so, the type of therapy to be provided (e.g., stimulation pulses).

For example, pacemakers typically employ one or more intravascular leads that connect to a so-called "can" containing a battery and associated electronics for pacing and sensing. Single-chamber pacemakers in the right atrium (RA) or right ventricle (RV) would typically be programmed in AAI or VVI modes, respectively, to inhibit pacing whenever intrinsic activity in that chamber is detected.

A dual-chamber pacemaker with RA and RV leads or a dual-chamber lead may have the ability to sense both atrial and ventricular electrical activity. For any patient with intermittent AV node conduction, it may be preferable to inhibit ventricular pacing and allow an intrinsic R wave to occur for a time after any P wave is detected on the RA lead. If ventricular pacing is needed, it is desirable to synchronize ventricular activity to atrial activity using an AV delay. The VDD programming mode has become common in dual-chamber pacemakers for patients with various degrees of AV block. Other common dual chamber modes include DDD and DDDR.

Current implantable medical devices (IMDs) for cardiac applications, such as pacemakers, include a "housing" or "can" and one or more electrically-conductive leads that connect to the can through an electro-mechanical connection. The can is implanted outside of the heart, in the pectoral region of the patient and contains electronics (e.g., a power source, microprocessor, capacitors, etc.) that provide pacemaker functionality. The leads traverse blood vessels between the can and heart chambers in order to position one or more electrodes carried by the leads within the heart, thereby allowing the device electronics to electrically stimulate or pace cardiac tissue and measure or sense myocardial electrical activity.

To sense atrial cardiac signals and to provide a right atrial chamber stimulation therapy, the can is coupled to an implantable right atrial lead including an atrial tip electrode that typically is implanted in the patient's right atrial appendage. The right atrial lead may also include an atrial ring electrode to allow bipolar stimulation or sensing in combination with the atrial tip electrode.

Before implantation of the can into a subcutaneous pocket of the patient, however, an external pacing and measuring device known as a pacing system analyzer (PSA) is used to ensure adequate lead placement, maintain basic cardiac functions, and evaluate pacing parameters for an initial programming of the device. In other words, a PSA is a system analyzer that is used to test how the leads would perform with an implantable device, such as an implantable pacemaker.

To sense right ventricular cardiac signals and provide ventricular stimulation therapy, the can is coupled to an implantable right ventricular lead including a right ventricular (RV) tip electrode and a right ventricular ring electrode. The lead for an implantable cardioverter defibrillator may also contain one or more electrodes for delivery of high-voltage therapy, such as a right ventricular coil electrode, a superior vena cava (SVC) coil electrode, or both. Typically, the right ventricular lead is transvenously inserted into the heart so as to place the right ventricular tip electrode in the right ventricular apex such that the RV coil electrode is positioned in the right ventricle and the SVC coil electrode is positioned in the right atrium and/or superior vena cava. Accordingly, the right ventricular lead is capable of receiving cardiac signals, and delivering stimulation in the form of pacing and shock therapy to the right ventricle.

A pacing system may also deliver resynchronization therapy, in which electrical stimulation is delivered to coordinate the electromechanical activity of the chambers of the heart. Such a pacing system may use the leads placed in the right atrium and right ventricle along with an additional lead coupled to the can that extends through the coronary sinus to a distal tip electrode on the outer surface of the left ventricle. There may be one or more ring electrodes in electrical contact with the left ventricle, the left atrium or both. The tip electrode may reach a location in the venous vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus.

Accordingly, the coronary sinus lead may be designed for some or all of the following functions: receive atrial and/or ventricular cardiac signals; deliver left ventricular pacing therapy using a left ventricular tip electrode for unipolar configurations or in combination with at least one left ventricular ring electrode for bipolar configurations; deliver left atrial pacing therapy using at least one left atrial ring electrode; deliver high-voltage therapy using at least one coil electrode.

Although a portion of the leads are located within the heart, a substantial portion of the leads, as well as the can itself are outside of the patient's heart. Consequently bacteria and the like may be introduced into the patient's heart through the leads, as well as the can, thereby increasing the risk of infection within the heart. Additionally, because the can is outside of the heart, the patient may be susceptible to Twiddler's syndrome, which is a condition caused by the shape and weight of the can itself. Twiddler's syndrome is typically characterized by subconscious, inadvertent, or deliberate rotation of the can within the subcutaneous pocket formed in the patient. In one example, a lead may retract and begin to wrap around the can. Also, leads may dislodge from the endocardium or veins and cause the device to malfunction. Further, in another typical symptom of Twiddler's syndrome, the device may stimulate the diaphragm, vagus, or phrenic nerve, pectoral muscles, or brachial plexus. Overall, Twiddler's syndrome may result in sudden cardiac arrest due to conduction disturbances related to the device.

In addition to the foregoing complications, implanted leads may experience certain further complications such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

To combat the foregoing limitations and complications, small sized devices configured for intra-cardiac implant have been proposed. These devices, termed leadless pacemakers (LLPM), are typically characterized by the following features: they are devoid of leads the pass out of the heart to another component, such as a pacemaker can outside of the heart; they include electrodes that are affixed directly to the can of the device; the entire device is attached to the heart; and the device is capable of pacing and sensing in the chamber of the heart where it is implanted.

LLPM devices that have been proposed thus far offer limited functional capability. These LLPM devices are able to sense in one chamber and deliver pacing pulses in that same chamber, and thus offer single chamber functionality. For example, an LLPM device is located in the right atrium would be limited to offering AAI mode functionality. An AAI mode LLPM can only sense in the right atrium, pace in the right atrium and inhibit pacing function when an intrinsic event is detected in the right atrium within a preset time limit. Similarly, an LLPM device that is located in the right ventricle would be limited to offering VVI mode functionality. A VVI mode LLPM can only sense in the right ventricle, pace in the right ventricle and inhibit pacing function when an intrinsic event is detected in the right ventricle within a preset time limit. To gain widespread acceptance by clinicians, would be highly desirable for LLPM devices to have dual chamber pacing/sensing capability (VDD or DDD mode) along with other features, such as rate adaptive pacing.

It has been proposed to implant sets of multiple LLPM devices within a single patient, such as when one or more LLPM devices located in the right atrium and one or more LLPM devices located in the right ventricle. The atrial LLPM devices and the ventricular LLPM devices wirelessly communicate with one another to convey pacing and sensing information there between to coordinate pacing and sensing operations between the various LLPM devices.

However, these sets of multiple LLPM devices experience various limitations. For example, if there is a wireless communication link between the devices, both devices must expend power to maintain the link. The wireless communication link should be maintained continuously in order to constantly convey pacing and sensing information between, for example, atrial LLPM device(s) and ventricular LLPM device(s). This exchange of pacing and sensing information is necessary to maintain continuous synchronous atrioventricular coordination.

Further, it is difficult to maintain a reliable wireless communications link between LLPM devices. The LLPM devices utilize low-power transceivers that are located in a constantly changing environment within the associated heart chamber. The transmission characteristics of the environment surrounding an LLPM device change due in part to the continuous cyclical motion of the heart and change in blood volume. Hence, the potential exists that the communication link is broken or intermittent.

SUMMARY

A summary of several sample aspects of the disclosure follows. It should be appreciated that this summary is provided for the convenience of the reader and does not wholly define the breadth of the disclosure. For convenience, one or more aspects or embodiments of the disclosure may be referred to herein simply as "some aspects" or "some embodiments."

The disclosure relates in some aspects to a leadless intracardiac medical device (LIMD) that is capable of sensing cardiac activity from multiple chambers, as well as applying cardiac stimulation to a cardiac chamber and/or generating a cardiac diagnostic indication. The LIMD is configured to be positioned entirely within an intra-cardiac space via transvenous implant. Access to an intra-cardiac space may be obtained by a delivery tool, such a sheath. The LIMD is sized to fit within and pass through the sheath so as to be placed within the intra-cardiac space. For example, the leadless device may be implanted within and in contact with one cardiac chamber (e.g., the RV) and detect near-field signals from that chamber as well as far-field signals from another chamber (e.g., the RA). Accordingly, for an RV or left ventricle (LV) leadless pacemaker, P waves, R waves and T waves may be distinguished using one or more of amplitude, timing, frequency content and associated mechanical activity.

In accordance with the teachings herein, even though the LIMD is in contact with a single cardiac chamber, the device is able to sense cardiac activity (e.g., electrical or mechanical activity) originating from other chambers and use the sensed information for advanced stimulation features and/or diagnostics. For example, a LIMD in the RV may use VDD mode with inhibited ventricular pacing when an R wave is detected, and use triggered RV pacing whenever a P wave is detected without a corresponding intrinsic ventricular activation. Also, sensed R-wave activity may be used for fusion or for predictive pre-pacing. In addition, sensed information may be used to optimize (e.g., reduce) ventricular pacing when possible. The teachings herein also may be employed with DDD or DDDR modes. Advantageously, a LIMD may be of sufficient size (e.g., wider than an implantable cardiac lead) to easily accommodate multiple electrodes. Moreover, in some cases (e.g., for far-field sensing), two or more of these electrodes may be spaced relatively far apart (e.g., by 1 millimeter or more). Consequently, a LIMD implemented in accordance with the teachings herein may more effectively provide advanced stimulation features and/or diagnostics as compared to lead-based systems.

The disclosure relates in some aspects to a LIMD that extends from one cardiac chamber to another to enable the sensing of cardiac activity from multiple chambers and applying cardiac stimulation to at least one cardiac chamber. For example, a LIMD attached in one chamber may include a structural member that is configured to extend into an adjacent chamber, whereby the structural member includes one or more electrodes for sensing and/or pacing. As another example, a LIMD attached in one chamber may be configured (i.e., elongated) such that a section of the device extends into an adjacent chamber, whereby one section of the device includes one or more electrodes for sensing and/or pacing in one chamber while another section of the device includes one or more electrodes for sensing and/or pacing in another chamber.

The disclosure relates in some aspects to a LIMD that monitors cardiac mechanical action. Accordingly, the leadless device may sense ventricular and atrial cardiac activity to provide cardiac stimulation without using electrical sensing.

The disclosure relates in some aspects to a LIMD that senses cardiac activity originating from multiple chambers and uses the sensed information to generate a cardiac diagnostic indication. For example, in some embodiments, a LIMD analyzes timing intervals of cardiac events from different chambers to determine whether a patient is suffering from first degree, second degree, or third degree heart block. Based on this determination, the leadless device generates an appropriate indication of heart block, if applicable.

BRIEF DESCRIPTION OF THE DRAWINGS

These and other aspects of the disclosure will be more fully understood when considered with respect to the following detailed description, the appended claims, and the accompanying drawings, wherein:

Figure 1:
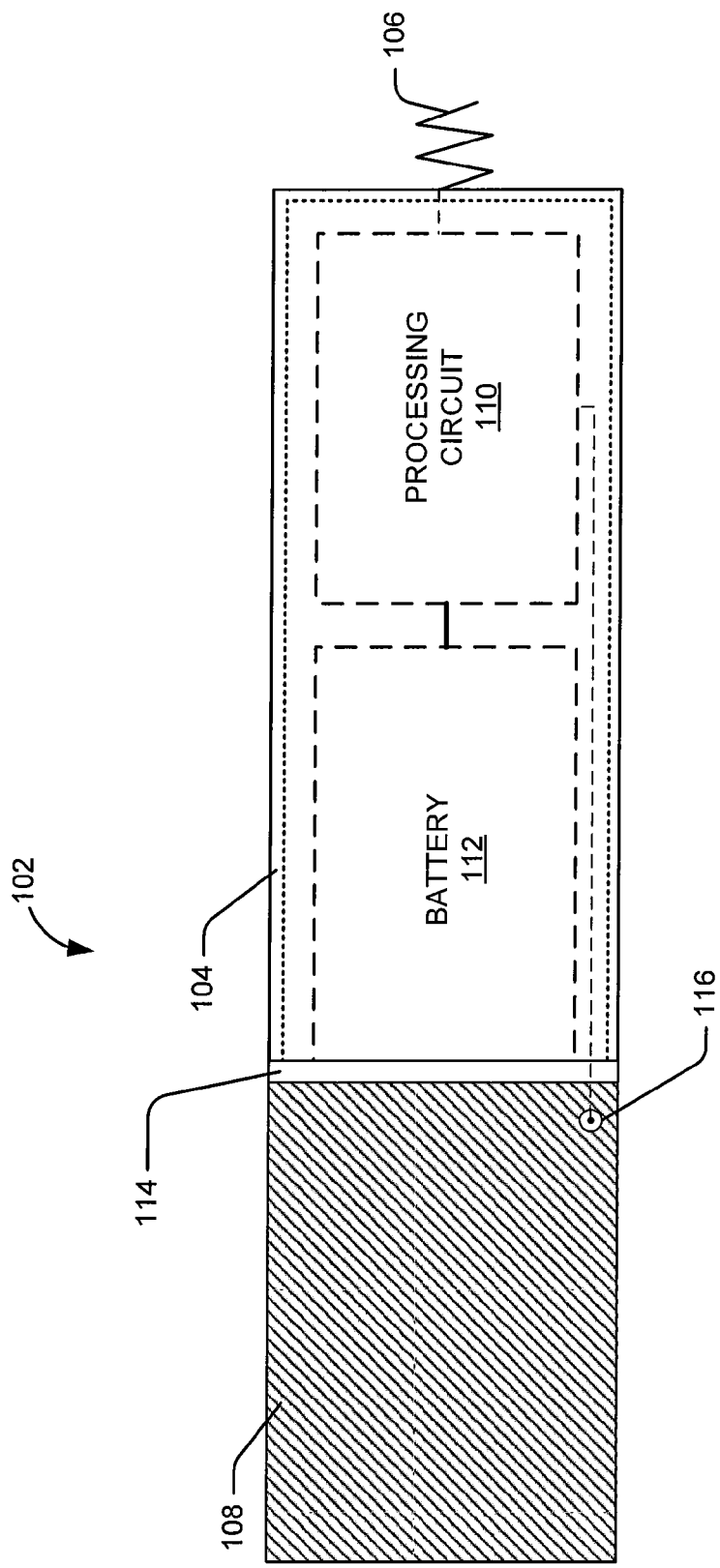
FIG. 1 is a simplified diagram of an embodiment of a leadless intra-cardiac medical device (LIMD)

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates an embodiment of a leadless intra-cardiac medical device (LIMD) 102 comprising a housing 104, an electrode 106 (e.g., a helical electrode), an electrode 108, and internal circuitry including a processing circuit 110 and a battery 112. As indicated by the dashed lines, the processing circuit 110 and a battery 112 are located within an interior space of the housing 104. Of note, the LIMD 102 does not include any implantable leads or any connectors for implantable leads.

Instead, in some embodiments, the LIMD 102 uses one or more of the electrodes 106 and 108 for directly delivering stimulation signals (e.g., pacing pulses) to cardiac tissue. For example, in some implementations, the electrode 106 acts as a cathode and the electrode 108 acts as an anode. As another example, in some implementations, the electrode 106 acts as cathode and the housing 104 (e.g., comprising a conductive material) acts as the anode.

The LIMD 102 also uses the electrodes 106 and 108 for sensing cardiac activity. For example, in some implementations, the electrode 106 is used for acquiring near-field signals while the electrode 108 is used for acquiring far-field signals. For sensing, the housing 104 (e.g., comprising a conductive material) and/or the other electrode may act as a reference electrode (e.g., ground). As used herein, the term near-field signal refers to a signal that originates in a local chamber (i.e., the same chamber) where the corresponding sense electrodes are located. Conversely, the term far-field signal refers to a signal that originates in a chamber other than the local chamber where the corresponding sense electrodes are located.

Figure 4:
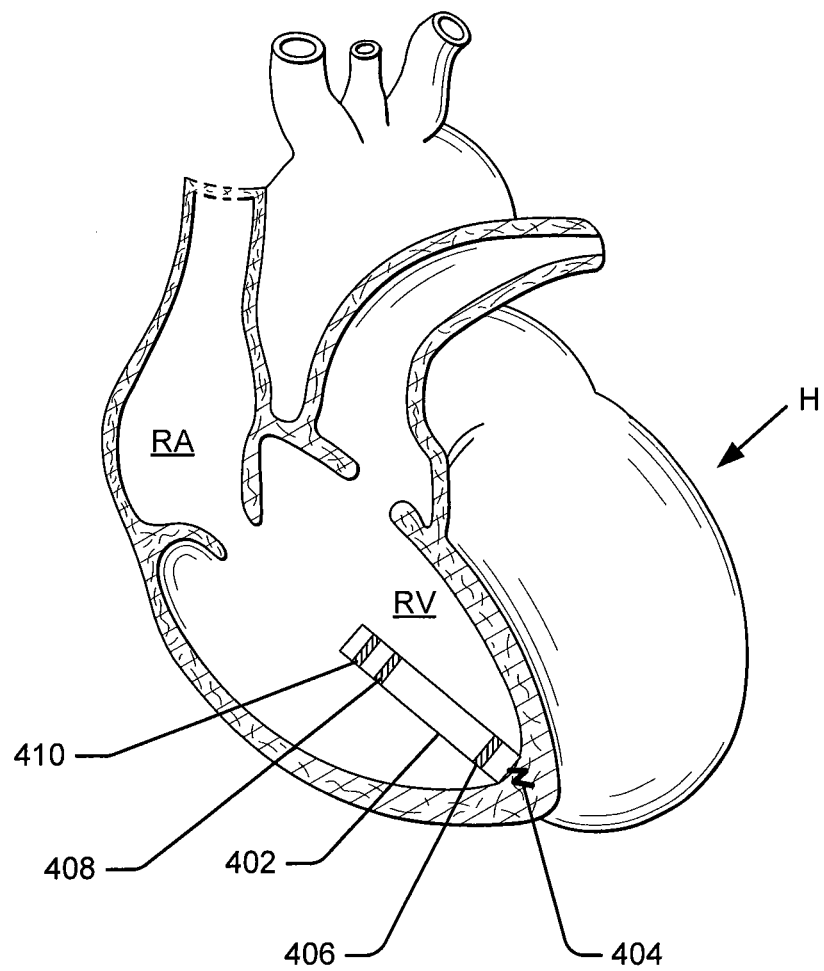
FIG. 4 is a simplified diagram of an embodiment of a LIMD implanted in a patient's heart for sensing conditions in the patient, delivering therapy to the patient, or providing some combination thereof.

Here, depending on the ratio of electrode surface areas, spacing between electrodes, and tissue contact, a pair of electrodes may be employed to effectively sense both near-field and far-field electrical activity. In some implementations (e.g., as depicted in FIG. 4), a LIMD may be implanted with an electrode used as the cathode in pacing attached endocardially to the myocardium of the heart and an electrode used as the anode protruding into a chamber of the heart. In some implementations, a LIMD may be implanted with the cathode attached at the epicardial surface of the heart and the anode on the other external face of the device. Because of the larger surface area of the anode and its contact to low-impedance fluid, the sensed electrical activity will include a significant far-field component that has less high-frequency content (in addition to the near-field signal of electrical activity near the cathode).

Through the use of a LIMD as taught herein, robust forms of therapy may be provided for a patient. For example, the LIMD 102 may be configured to provide VDD mode pacing, VVI mode pacing, and other pacing modes.

As discussed in more detail below, the processing circuit 110 includes various circuitry for acquiring and processing signals indicative of cardiac activity and for applying stimulation signals to cardiac tissue. For example, for sensing operations, at least one sensing circuit is coupled to one or more of the electrodes 106 and 108 for measuring cardiac electrical activity. In addition, for stimulation operations, at least one signal generator circuit is coupled to one or more of the electrodes 106 and 108 for stimulating cardiac tissue.

In the example of FIG. 1, the electrode 108 may be implemented as forming part of the housing 104 or may be implemented upon (i.e., around) a recessed section of the housing 104. In the latter case, if the housing 104 is conductive, the electrode 108 lies on top of an insulator (not shown) that separates the bottom surface of the electrode 108 from an upper surface of the housing 104.

To facilitate long-term implant within a patient, all external surfaces and materials of the LIMD 102 comprise biocompatible materials. For example, the housing 104 may be constructed of titanium, a ceramic material, or some other suitable biocompatible material. The electrodes 106 and 108 may be constructed of titanium or some other suitable conductive and biocompatible material. In addition, insulators (e.g., insulator 114) may be constructed of ceramic, polyurethane, silicone or some other suitable electrically insulating and biocompatible material.

Also to facilitate long-term implant, the LIMD 102 is hermetically sealed. To this end, hermetically sealed feedthroughs (e.g., feedthrough 116) are employed in some embodiments to electrically couple the electrodes 108 and 106 to internal conductors of the LIMD 102 (represented by dashed lines in FIG. 1). Alternatively, feedthroughs may not be employed in embodiments where the electrode 108 is part of the hermetic housing (e.g., if the insulator 114 and/or the housing 104 is made of ceramic, sapphire, or some other hermetic insulator material). In such a case, an electrical connection may be made to an interior surface of the electrode 108.

In some embodiments, the LIMD 102 is sized to facilitate venous-based implant to a single cardiac chamber (e.g., the RV). For example, the housing 104 may have a cross-sectional width (e.g., diameter) of less than 6 millimeters in some embodiments. In addition, to accommodate the internal circuitry (in particular, the battery 112, e.g., which may extend into the interior space under the electrode 108), the housing 104 may have a length of at least 30 millimeters in some embodiments. It should be appreciated, however, that in other embodiments, the width will be greater than or equal to 6 millimeters and/or the length will be less than or equal to 30 millimeters.

In some embodiments it is desirable to place the proximal electrodes as close to an adjacent chamber as possible (e.g., to facilitate far-field sensing). In such a case, the housing 104 may have a length of 60 millimeters or more.

Figure 2:
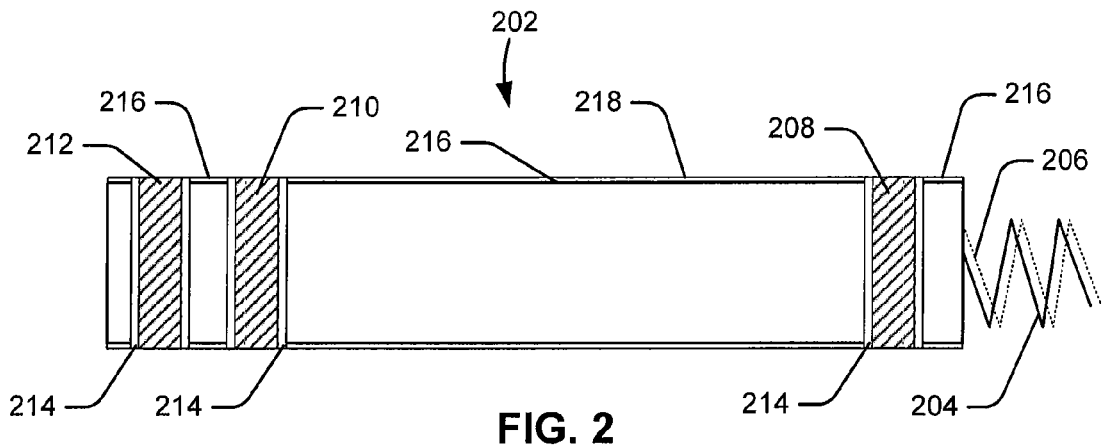
FIG. 2 is a simplified diagram of an embodiment of a LIMD comprising multiple electrodes for near-field sensing and multiple electrodes for far-field sensing.
Figure 3:
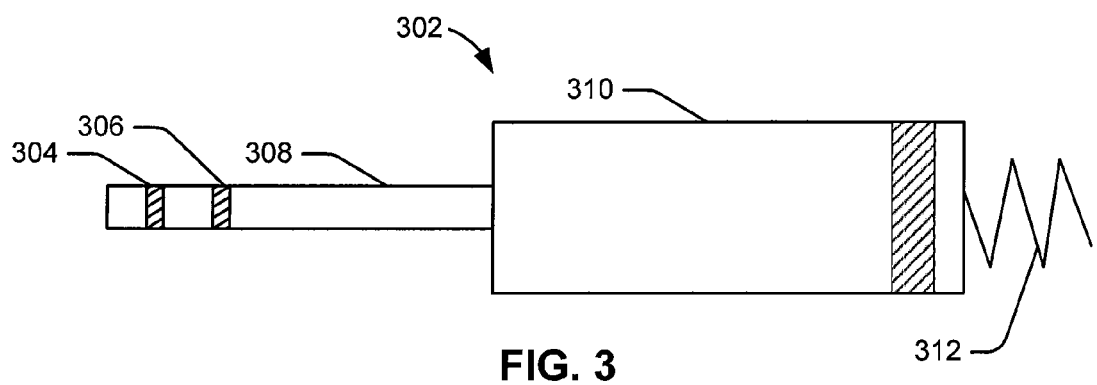
FIG. 3 is a simplified diagram of an embodiment of a LIMD comprising an elongated structural member that includes at least one electrode for far-field sensing.

The electrodes of a LIMD may take various forms in various implementations. FIGS. 2 and 3 illustrate several examples of other electrode configurations that may be employed independently or in combination with one another on a LIMD as taught herein.

FIG. 2 illustrates two alternative embodiments that employ a bipolar pair of electrodes for near-field sensing and/or for direct tissue stimulation. The LIMD 202 includes a helix electrode 204 that protrudes from the distal end of the LIMD 202. In addition, in different embodiments, the LIMD 202 includes either another helix electrode 206 or a ring electrode 208. Thus, in one embodiment, a bipolar electrode pair consists of the electrodes 204 and 206, while in another embodiment, a bipolar electrode pair consists of the electrodes 204 and 208.

FIG. 2 also illustrates that in some embodiments a bipolar pair of electrodes is used for far-field sensing. In this example, ring electrodes 210 and 212 are provided at a proximal section of the LIMD 202.

FIG. 2 illustrates that in some embodiments all or a portion of the housing 216 may be covered with or comprise an insulating material 218. This insulating material (e.g., composed of parylene) may be employed to prevent electrical conduction between conductive surfaces of the LIMD 202 (e.g., the ring electrodes and, in some cases, a conductive housing). For example, relatively thin insulators 214 may be employed between the ring electrodes and the housing 204 (e.g., constructed of titanium) of the LIMD 202. Since the LIMD 202 is typically in contact with conductive fluid, there is a potential for electrical conductivity across the small gap provided by the thin insulators 214. Accordingly, this electrical conductivity may be eliminated by employing an insulating material 218 on the surface of the housing 216 between the conductive surfaces of the LIMD 202. In some embodiments, package segments between electrode rings comprise an insulating material (e.g., sapphire, ceramic, etc.). This may provide a simpler package design that costs less to produce.

The electrodes that are used for far-field sensing (e.g., the proximal electrodes) may be configured to facilitate such sensing. For example, each of these electrodes may have a relatively large surface area (e.g., 2-30 square centimeters) in some embodiments. As another example, the distance between the electrodes may be relatively large (e.g., at least 15 millimeters) in some embodiments.

FIG. 3 illustrates an embodiment of a LIMD 302 where electrodes 304 and 306 are incorporated into a structural member 308 that extends from the housing 310 of a LIMD 302. Such a structural member may be employed, for example, to position one or more electrodes in closer proximity to another chamber of the heart. For example, an electrode 312 at a distal section of the LIMD 302 may be attached to the apex of the RV upon implant (e.g., in a similar manner as shown in FIG. 4). In this case, the structural member 308 and, hence, the electrodes 304 and 306 will extend toward the RA. Consequently, the LIMD 302 may be able to more effectively sense cardiac activity that originates in the RA. In some embodiments, the structural member 308 may have a length of at least 30 millimeters. The structural member 308 may be composed of Nitinol, polyurethane, or some other suitable biocompatible material.

FIG. 4 illustrates an example of how a LIMD 402 may be implanted in a chamber of a heart H. Here, the LIMD 402 is implanted in the heart H such that no part of the LIMD 402 is located in a cardiac chamber from which far-field signals originate (e.g., an atrial chamber).

In this example, a distal section of the LIMD 402 comprises a helix electrode 404 that is actively affixed to an inner wall of the RV. The helix electrode 404 in combination with a ring electrode 406 is used for near-field sensing of RV events. In addition, bipolar electrodes 408 and 410 at a proximal section of the LIMD 402 are employed for far-field sensing of RA events and/or other cardiac events. Here, the electrodes 408 and 410 may be optimized for such far-field sensing based on, for example, one or more of: placement of the electrodes 408 and 410 at a proximal section of the LIMD 402, increased spacing between the electrodes 408 and 410, or increased sizing of the electrodes 408 and 410.

In some embodiments, the LIMD comprises at least one mechanical support (e.g., attachment) structure. A mechanical support structure is employed to assist in holding the LIMD in place within the heart upon implant.

Figure 5:
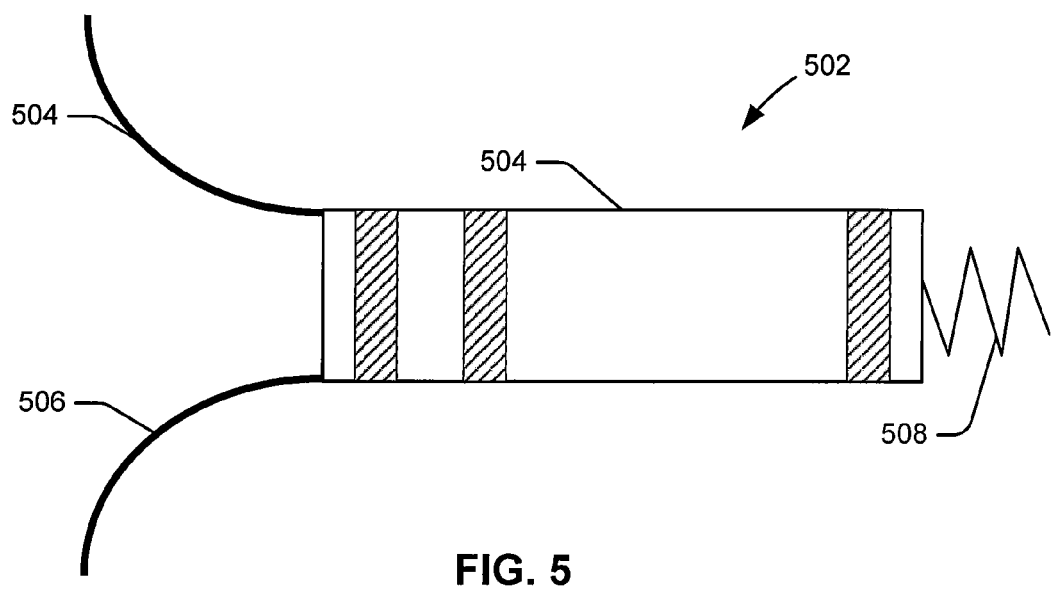
FIG. 5 is a simplified diagram of an embodiment of a LIMD comprising elongated mechanical support structures.

FIG. 5 illustrates an embodiment of a LIMD 502 comprising a pair of flexible mechanical support structures 504 and 506. The mechanical support structures 504 and 506 are shown in their unconstrained orientation. That is, in the absence of any external force, the mechanical support structures 504 and 506 are predisposed to bend outward. During the implant procedure, the mechanical support structures 504 and 506 are bent inwards (i.e., compressed toward one another) to facilitate delivery of the LIMD 502 within a removable implant sleeve or other similar structure. Thus, upon implant within a chamber (e.g., upon withdrawal of the implant sleeve), the mechanical support structures 504 and 506 will expand apart from one another and exert forces on opposite walls of the cardiac chamber, thereby helping to hold the LIMD 502 in place within the chamber.

A mechanical support structure as taught herein may take different forms in different implementations. For example, as discussed above, a mechanical support structure (e.g., multiple attachment members working in cooperation) may be predisposed to rest against multiple inner walls of a heart. As another example, a mechanical support structure may be configured to facilitate passive or active attachment to an inner wall. A mechanical support structure may be composed of Nitinol, polyurethane, or some other suitable biocompatible material.

Figure 6:
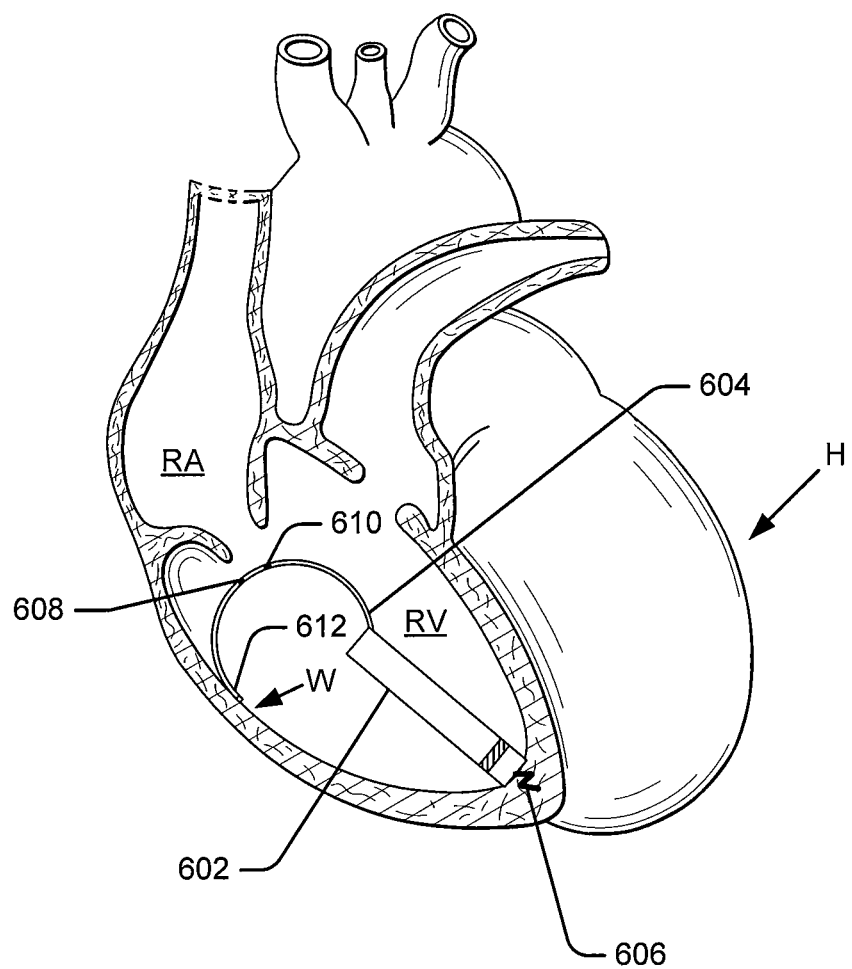
FIG. 6 is a simplified diagram of an embodiment of a LIMD comprising an elongated mechanical support structure and implanted in a patient's heart.

FIG. 6 illustrates an example of how a LIMD 602 comprising a mechanical support structure 604 may be implanted in a chamber of a heart H. Here, the mechanical support structure 604 is predisposed such that in an unconstrained orientation (e.g., after removal of the implant sleeve), an end section 612 of the mechanical support structure 604 rests against an inner wall W of the RV. This end section may thus be actively attached to the inner wall W (e.g., via a mechanical or chemical-based attachment technique) and/or eventually become passively attached to the inner wall W (e.g., by buildup of intima over the end section 612). Thus, the LIMD 602 may be held relatively firmly in place by action of the mechanical support structure 604 and by action of the helix structure 606 at the distal section of the LIMD 602.

FIG. 6 also illustrates that a mechanical support structure may comprise one or more electrodes. In this example, electrodes 608 and 610 are positioned along the mechanical support structure 604 such that the electrodes 608 and 610 are in relatively close proximity to the RA to facilitate sensing cardiac signals that originate in the RA. The electrodes 608 and 610 are electrically coupled to the internal circuitry (not shown) of the LIMD 602 via conductors (not shown) that are incorporated into the mechanical support structure 604.

Figure 7:
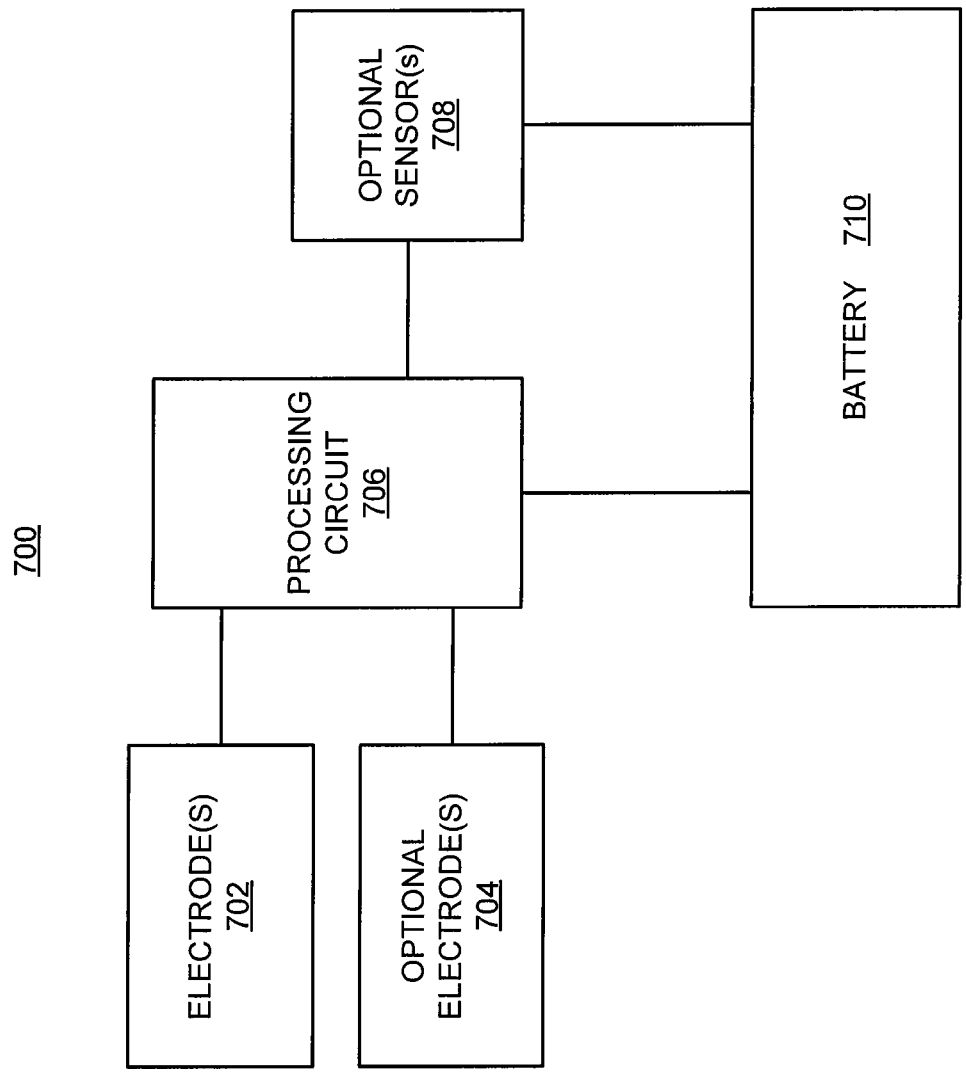
FIG. 7 is a simplified block diagram of an embodiment of circuitry for a LIMD.

FIG. 7 illustrates examples of circuitry 700 that may be employed in a LIMD in accordance with the teachings herein. For purposes of illustration, the circuitry 700 is depicted as including at least one electrode 702, a processing circuit 706, and a battery 710; and optionally including at least one electrode 704 and at least one sensor 708. As discussed herein, different combinations of these components may be employed in an embodiment that relies solely on electrical sensing, an embodiment that relies on electrical sensing and at least one other type of sensing (e.g., mechanical sensing), or an embodiment that does not rely on electrical sensing (e.g., an embodiment that only employs mechanical sensing).

At least one electrode 702 is used for stimulating cardiac tissue. For example, the at least one electrode 702 may correspond to the electrode(s) at the distal section of a LIMD. In some implementations, one or more of the at least one electrode 702 also may be used for sensing cardiac activity (e.g., near-field sensing). In some embodiments (e.g., the embodiment of FIGS. 1-3), at least one electrode 704 is used for sensing cardiac activity (e.g., far-field sensing). In some implementations, one or more of the at least one electrode 704 also may be used for stimulating cardiac tissue.

In some embodiments, the circuitry 700 includes at least one sensor 708. For example, some embodiments that identify cardiac events based at least on part on mechanical cardiac activity will include one or more electro-mechanical sensors.

The processing circuit 706 is electrically coupled to each electrode 702 and 704, when present, to receive electrical signals indicative of cardiac activity for sensing operations, and to supply stimulation signals to cardiac tissue during stimulation operations. In addition, in embodiments that employ at least one sensor 708, the processing circuit 706 is electrically coupled to each sensor 708 to receive electrical signals indicative of cardiac activity. To facilitate interfacing with these components, the processing circuit 706 may comprise one or more of: a sensing circuit, an amplifier, a filter, a signal generator, a signal driver, a switching circuit, or other suitable circuits. Thus, the processing circuit 706 may filter, amplify, and detect signals received from one or more electrodes and/or one or more sensors. In addition, the processing circuit 706 may generate, filter, and amplify signals sent to one or more electrodes.

The processing circuit 706 processes received signals to identify cardiac events. For example, a microprocessor of the processing circuit 706 may be configured to acquire intracardiac electrogram data (and/or other cardiac related signal data) and identify P waves, R waves, T waves and other cardiac events of interest. Based on analysis of these cardiac events, the processing circuit may selectively generate stimulation signals (e.g., pacing pulses) to be delivered to cardiac tissue via one or more electrodes. Sample operations relating to the processing of sensed signals and the generation of stimulation signals by a LIMD will be described in more detail in conjunction with the flowchart of FIG. 8.

Figure 8:
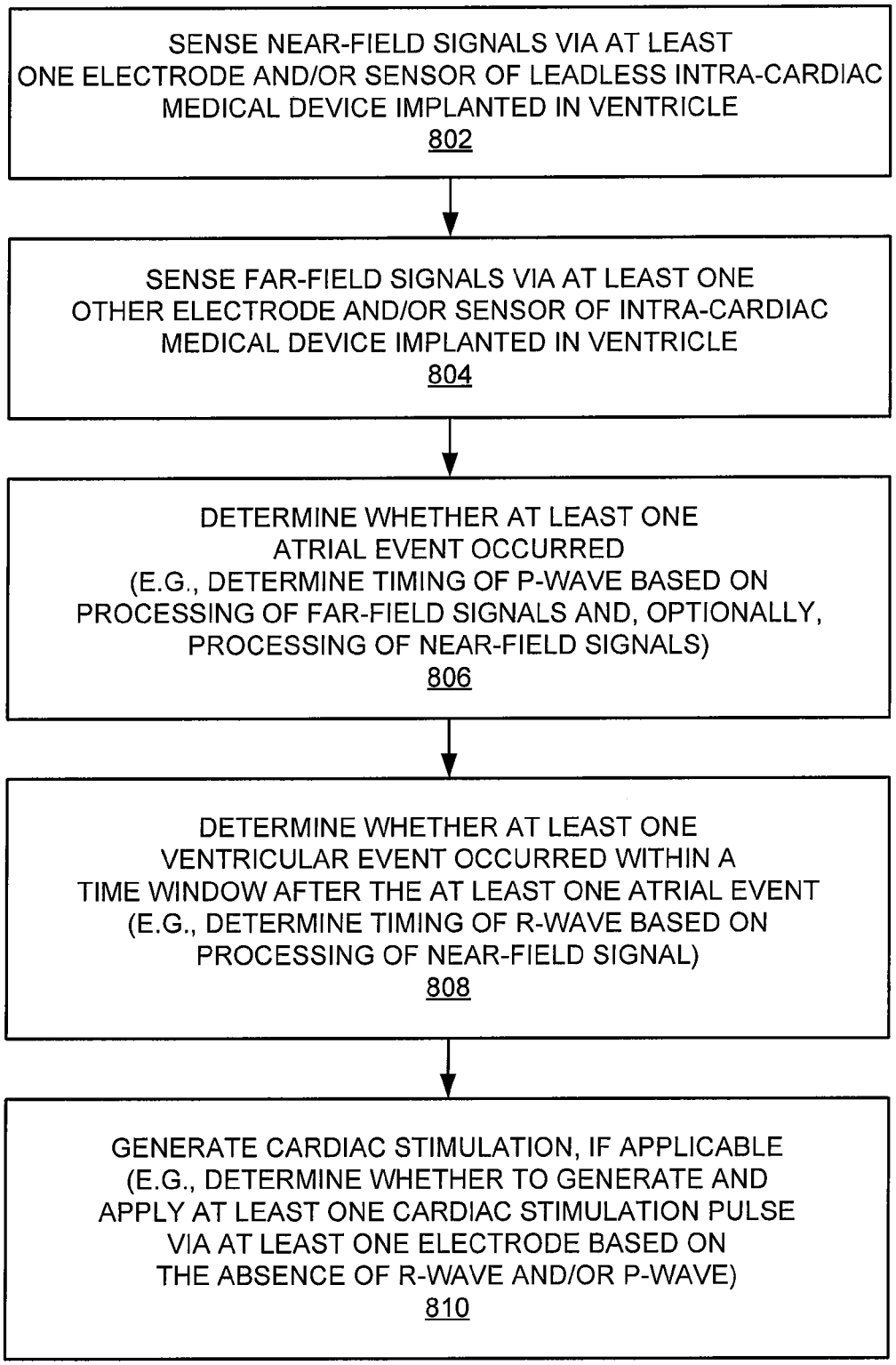
FIG. 8 is a simplified flowchart of an embodiment of operations that may be performed by, for example, circuitry of a LIMD.

For convenience, the operations of FIG. 8 (or any other operations discussed or taught herein) may be described as being performed by specific components (e.g., the components of FIG. 7). It should be appreciated, however, that these operations may be performed by other types of components and may be performed using a different number of components. It also should be appreciated that one or more of the operations described herein may not be employed in a given implementation.

As represented by block 802 of FIG. 8, near-field signals are sensed in a ventricle. As discussed herein, in some embodiments, the signals are sensed via at least one electrode and/or at least one sensor (e.g., electro-mechanical sensor) of a LIMD implanted in the ventricle.

As represented by block 804, far-field signals are sensed in the ventricle. Again, the signals may be sensed via at least one electrode and/or at least one sensor (e.g., electro-mechanical sensor) of the LIMD implanted in the ventricle.

As represented by blocks 806 and 808, a processing circuit of the LIMD determines whether at least one atrial event occurred and whether at least one ventricular event occurred based on the sensed far-field signals and the sensed near-field signals, respectively. For example, for a given cycle, the processing circuit determines if an atrial event occurred and if a ventricular event occurred within a time window after the atrial event.

The occurrence and timing of an R wave may be identified based on processing of the near-field signals. In addition, the occurrence and timing of a P wave may be identified based on processing of the far-field signals and, optionally, the processing of the near-field signals. As an example of the latter scenario, the circuitry used for sensing for the P wave may be set to high gain to enable the relatively small P wave to be detected from the far-field signals. This may result a large-amplitude signal, possibly even saturation at the time of the R wave in the far-field signals. However, the R wave can be readily eliminated from consideration here since the timing of the R wave is known from the processing of the near-field signals.

As another example, the occurrence and timing of a P wave may be identified by filtering the far-field signals using different bandwidths (e.g., via a narrow-bandwidth filter and a wider-bandwidth filter). Here, the narrow filtering operation (e.g., employing a bandwidth of 20-100 Hz) may provide an output dominated by the R wave, while the wider filtering operations (e.g., employing a bandwidth of 2-150 Hz) may provide an output that includes both the R wave and the P wave. Accordingly, the presence and timing of a P wave may be identified by comparing the filtered far-field signals.

As yet another example, the identification of a cardiac event may be based on the use of morphology templates. For example, the determination as to whether the at least one ventricular event occurred may involve correlating a morphology derived from the near-field signals with at least one ventricular morphology template. Similarly, the determination of whether the at least one atrial event occurred may involve correlating a morphology derived from the far-field signals with at least one atrial morphology template.

As represented by block 810, the processing circuit generates cardiac stimulation (e.g., generate at least one cardiac stimulation pulse to the ventricular tissue) based on the determinations of blocks 806 and 808. For example, the processing circuit may determine whether to apply stimulation to cardiac tissue via at least one electrode of the LIMD based on whether an R wave and/or a P wave was detected within a defined window of time. In particular, stimulation is delivered to the ventricle if an R wave does not occur within a window of time after a P wave.

Several examples of operations that may be employed to perform the operations of blocks 806-810 follow. In particular, various components of a cardiac signal, including P waves, R waves, and T waves, may be distinguished using one or more of the techniques described below.

In some embodiments, amplitude window filtering is used to exclude the intrinsic R wave. The R wave is known to be a local signal with high amplitude during sinus rhythm. In contrast, the far-field P wave will have an amplitude that does not exceed an upper threshold, since it is recorded as a far-field signal. The gain of the sensing circuitry may be increased to resolve signals having lower amplitude, with the R wave allowed to go out of range.

In some embodiments, timing window filtering is used to exclude the T wave. Whenever an R wave is identified or a ventricular pulse is delivered, any activity following it is assumed to be the effect of ventricular repolarization. As an example, consider a leadless pacemaker set to pace the RV at a rate of 60 bpm. The window size for searching for a P wave may be set to an interval of 300-1000 ms after the prior R wave or V pacing pulse. If a P wave is detected in that window, the leadless pacemaker waits for the programmed AV interval to find an intrinsic R wave, before timing out and delivering a V pacing pulse. If a P wave does not occur in that window, the leadless pacemaker assumes that a P wave will not happen, and delivers a V pacing pulse at 1000 milliseconds. The window size may be programmable.

In some embodiments, electrical activity may also be manipulated by other filtering techniques, either in hardware or software. For example, sensing circuitry may be employed for wideband activity that includes components of lower frequencies, as well as for narrower-band activity that excludes lower-frequency components, for example by having a cutoff frequency that excludes content below 20 Hz. Any periodic, repeating segment on the narrower-band signal having an appreciable amount of higher-frequency activity is marked as R wave local ventricular activation. The wideband signal is then used, with the R wave periods excluded, to locate far-field atrial activity. As another example, a low-bandwidth filter that excludes higher-frequency local activation may be employed. The low-bandwidth version of the signal is used to detect far-field atrial activity.

Some embodiments may use morphology-based techniques to identify cardiac events. For example, whenever atrial activity originates from the same focal point (presumably the SA node) and propagates through the same conduction pathways, it will appear with a specific and measurable pulse shape recorded by the leadless pacemaker. The morphology of the P wave can thus be identified by the person using the programmer and separated from R and T waves upon programming the LIMD. Identification of P, R and T waves may be stored in morphology templates in the LIMD.

Some embodiments may employ rate response techniques. For example, an increase in atrial rate may be used to indicate that ventricular rate should also increase. If it is known that the atrial rate response is insufficient, the ventricle may be overdriven at an even faster rate whenever the atrial rate increases. Overdrive may involve loss of AV synchrony to achieve higher ventricular rate, or may take the form of delivery of additional ventricular pulses without altering AV synchrony. Similarly, if there is another activity sensor such as an accelerometer on the LIMD, information derived from this sensor may be used to determine whether to overdrive the ventricular rate or modify the AV delay whenever increased activity is warranted (e.g., upon increase in inotropic activity).

In some embodiments, a sensor such as an accelerometer is used for correlating cardiac electrical and mechanical activity. An attached LIMD in contact with the endocardial RV will remain in continual balance between the forces of contact with tissue and the motion of blood around it. When ventricular systole occurs, the mechanical contraction of the ventricles will cause sudden acceleration in a repeatable, measurable direction. When atrial systole occurs, there may also be related mechanical activity, blood motion or diastolic relaxation exerting motion on the sensor. This "intra-cardiac mechanogram" recorded on the accelerometer will have a signature with unique atrial and ventricular components. These components of mechanical action may be combined with the electrogram to distinguish P, R and T waves. If an apparent electrical activation occurs that is correlated to a mechanical action indicative of ventricular systole, that event is classified as ventricular.

As discussed herein, in some embodiments, a LIMD does not employ any type of cardiac electrical sensing. For example, an accelerometer may be incorporated into a leadless RV device positioned in such a way that it is able to detect atrial and ventricular mechanical activity. When atrial contraction is detected, the device uses the time of the event and a programmed mechanical-electrical AV delay to determine when and if ventricular pacing is needed. If a ventricular contraction occurs before the end of the programmed AV delay, the device does not deliver any electrical stimulation.

In some embodiments, a sensing circuit is used to facilitate delivering fusion pacing. When a sensed R wave begins to occur, the LIMD delivers a pacing spike at a time programmed to deliver a blended intrinsic-paced event. If no R wave is sensed within the programmed time window, the LIMD delivers a paced pulse to ensure ventricular capture.

In some embodiments, a LIMD may deliver predictive pre-pacing. If there is a LIMD in the LV, but it is desired to pre-pace the LV before RV activation occurs, several test beats of entirely intrinsic activity will be sensed. The interval between R waves is measured. As an example, the interval may be consistently 1000 ms and it may be desired to pre-pace the LV by 50 milliseconds. In this case, after the test period of sensing intrinsic activity expires, the LIMD may wait 950 ms after the last measured R wave before delivering LV pacing. Similarly, the AV interval may be measured during intrinsic ventricular activity, with pre-pacing of the LV delivered based on a time interval after atrial activation. Whenever it is uncertain if pre-pacing continues to work correctly, it may be stopped for one or more beats. If the sensed R wave does not occur at the anticipated time, several more test beats may be used to recalibrate the pacing. Additionally, the sensing circuitry may be used to measure the evoked response. The device may also be programmed to note the morphology when pre-pacing occurs at the appropriate time and to detect, by a change in morphology, when it needs to have its predictive pre-pacing recalibrated.

Figure 9:
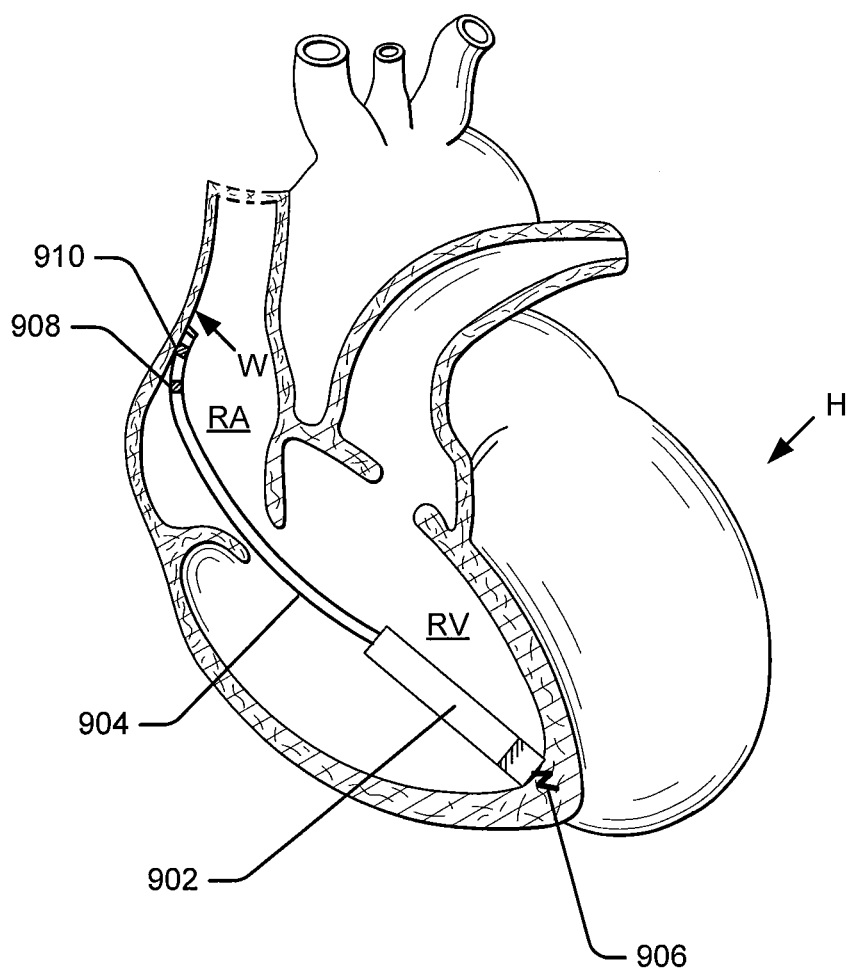
FIG. 9 is a simplified diagram of an embodiment of a LIMD comprising an elongated structural member and implanted in a patient's heart.

Referring now to FIG. 9, in some embodiments, a LIMD comprises an elongated structural member that is configured (e.g., sized) to extend into another cardiac chamber. Such a structural member may be used, for example, for one or more of: sensing in the other chamber, applying stimulation in the other chamber, or facilitating attachment of the LIMD within the heart.

FIG. 9 illustrates an embodiment of a LIMD 902 implanted in the RV and comprising an elongated structural member 904 that extends into the RA. The elongated structural member 904 is predisposed such that in an unconstrained orientation (e.g., after removal of the implant sleeve), an end section of the elongated structural member 904 rests against an inner wall W of the RA. This end section may thus be actively attached to the inner wall W and/or eventually become passively attached to the inner wall W (e.g., as discussed above). Thus, the LIMD 902 may be held relatively firmly in place by action of the elongated structural member 904 and by action of the helix structure 906 at the distal section of the LIMD 902. The elongated structural member 904 may be composed of Nitinol, polyurethane, or some other suitable biocompatible material.

FIG. 9 also illustrates that a structural member may comprise one or more electrodes. In this example, electrodes 908 and 910 are positioned along the elongated structural member 904 such that the electrodes 908 and 910 effectively sense cardiac signals that originate in the RA. In some embodiments, the electrodes 908 and 910 are also used for stimulating the RA (e.g., applying pacing pulses). The electrodes 908 and 910 are electrically coupled to the internal circuitry (not shown) of the LIMD 902 via conductors (not shown) that are incorporated into the elongated structural member 904. In some implementations, the LIMD 902 may be employed to support DDD, DDDR, or other modes.

The elongated structural member 904 is configured to facilitate implantation across an inter-chamber valve (e.g., the tricuspid valve) of the heart. For example, the size (e.g., a cross-sectional dimension of less than 6 millimeters) and flexibility of the elongated structural member 904 may be defined to mitigate any negative impact that the presence of the elongated structural member 904 will have on the operation of the valve.

Figure 10:
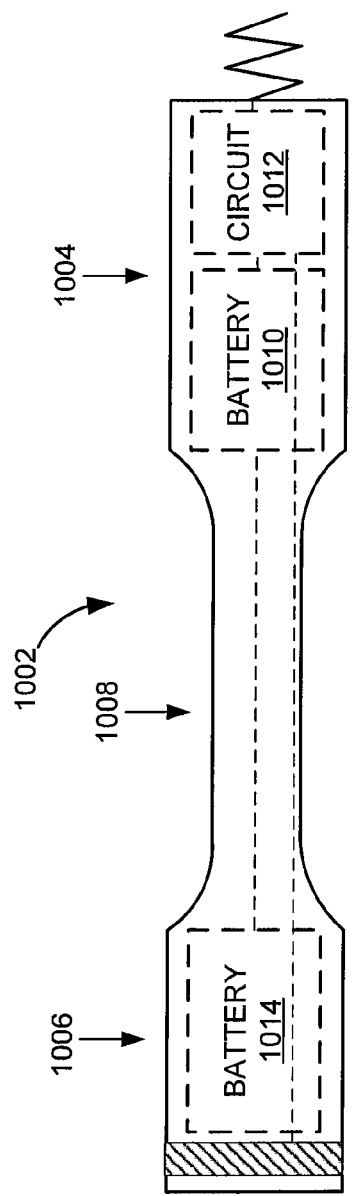
FIG. 10 is a simplified diagram of an embodiment of a LIMD configured to extend between multiple cardiac chambers.

FIG. 10 illustrates another embodiment of a LIMD 1002 that is configured (e.g., proportioned) to extend into multiple cardiac chambers. The LIMD 1002 includes two wider (e.g., in cross-sectional dimension) outer sections 1004 and 1006, and a narrower inner section 1008. Here, the inner section 1008 is configured to facilitate implantation of the LIMD 1002 across an inter-chamber valve (e.g., the tricuspid valve) of the heart. For example, upon implant, the section 1004 may be affixed in the RV and the section 1006 placed in the RA. Consequently, the location (e.g., distance from the distal end), the size (e.g., a cross-sectional dimension of less than 6 millimeters), and flexibility of the inner section 1008 may be defined to ensure that only the inner section 1008 will lie within the valve after implant and to mitigate any negative impact that the presence of the inner section 1008 will have on the operation of the valve.

FIG. 10 also illustrates that the larger circuitry of the LIMD 1002 may be located within the wider sections of the LIMD 1002. For example, the outer section 1004 (e.g., the distal section) may include a battery 1010 and other circuitry 1012 (e.g., a processing circuit, sensors, etc.), while the outer section 1006 (e.g., the proximal section) may include a battery 1014 and other circuitry (not shown).

Figure 11:
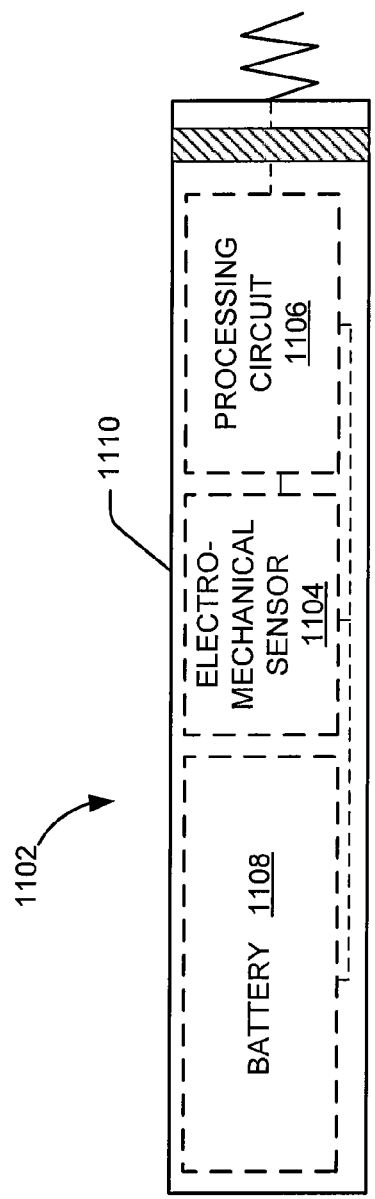
FIG. 11 is a simplified diagram of an embodiment of a LIMD that employs mechanical sensing and no electrical sensing.

In some embodiments, a LIMD advantageously employs mechanical sensing rather than electrical sensing to identify cardiac events. Thus, such an embodiment need not employ sensing electrodes, electrical sensing circuitry, and corresponding electrical signal processing to detect far-field (and near-field) cardiac activity. FIG. 11 illustrates an embodiment of a LIMD 1102 comprising at least one electro-mechanical sensor 1104, a processing circuit 1106 electrically coupled to receives signals from the at least one electro-mechanical sensor 1104, and a battery 1108 that are located within an interior space of a housing 1110.

The electro-mechanical sensor 1104 generates signals that may be used to identify a cardiac event (e.g., ventricular event and/or atrial event). The processing circuit 1106 may then process these signals to determine whether certain cardiac events occurred. Based on this determination, the processing circuit 1106 may generate signals for stimulating cardiac tissue.

For example, testing or simulations may be employed to identify the different forms, timing, and amplitudes of mechanical activity associated with different types of cardiac events. This information may then be stored in a memory device (e.g., of the processing circuit 1106). Similar information may then be obtained from the electro-mechanical sensor 1104 during normal monitoring of the patient. Mechanical activity information derived from different portions of the signals from the electro-mechanical sensor 1104 may then be correlated with the stored information (e.g., a ventricular mechanical activity template and/or an atrial mechanical activity template) to determine whether and when a particular type (e.g., ventricular or atrial) of cardiac event occurred.

Cardiac event information acquired via the mechanical sensing may be used for cardiac stimulation operations in accordance with the teachings herein and/or conventional cardiac signal processing techniques. For example, upon identifying the timing of an R wave (e.g., which may manifest itself as a relatively large and, hence, easily identifiable mechanical event), a timing window may be employed to identify the timing of a P wave that preceded the R wave (e.g., within a timing range as indicated by the timing window).

The at least one electro-mechanical sensor 1104 may take various forms in different implementations. In some embodiments, the at least one electro-mechanical sensor 1104 comprises at least one accelerometer that is configured to measure acceleration in different directions. In this way, more precise information may be obtained regarding all cardiac event of interest.

Figure 12:
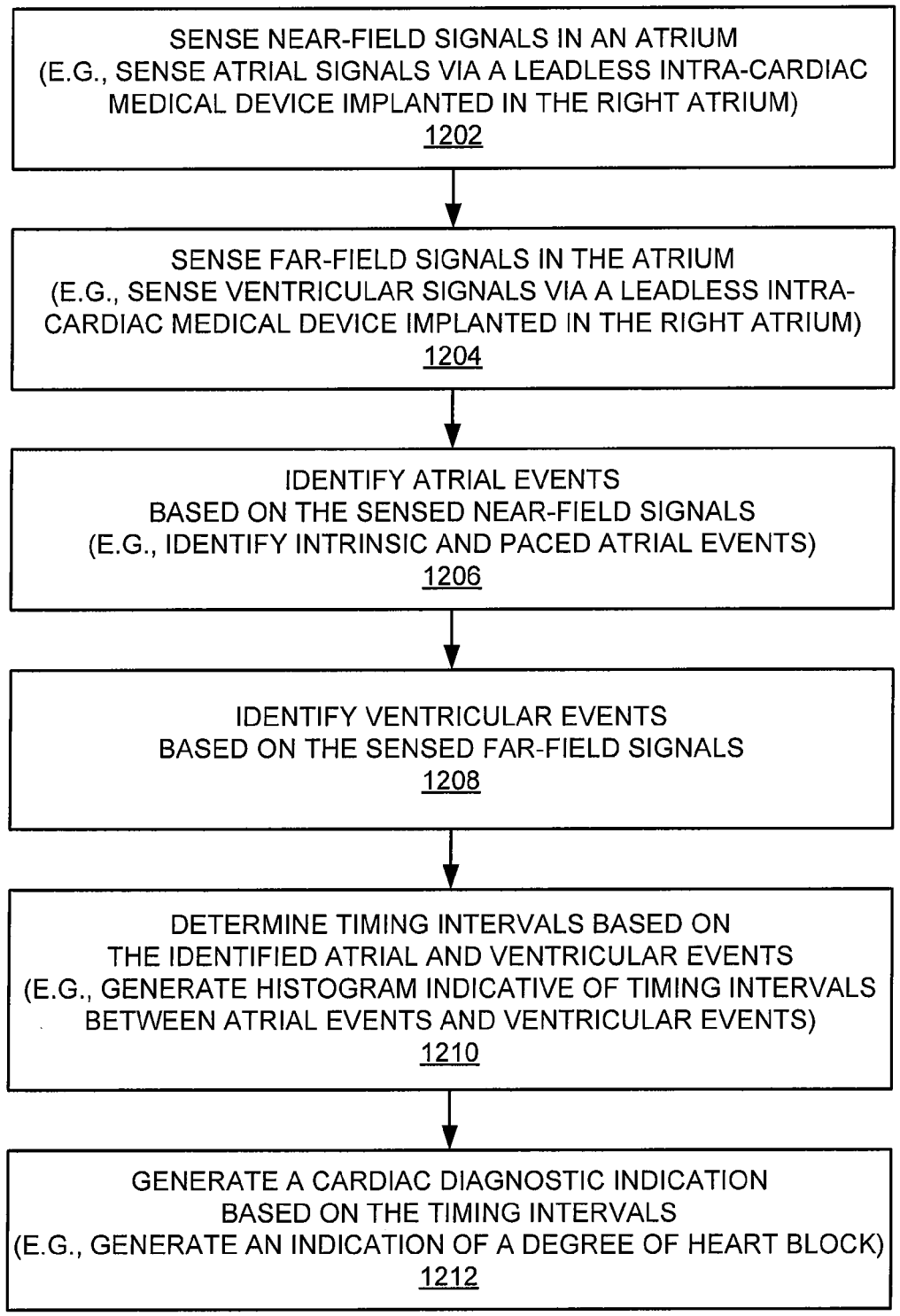
FIG. 12 is a simplified flowchart of an embodiment of cardiac diagnostic operations that may be performed by, for example, circuitry of a LIMD.

As mentioned above, the disclosure also relates in some aspects to a LIMD that senses cardiac activity from multiple chambers to generate a cardiac diagnostic indication. For example, a LIMD may be implanted within one cardiac chamber (e.g., the RA), and include circuitry for sensing near-field signals from that chamber and for sensing far-field signals from another chamber (e.g., the RV). As discussed herein, the circuitry may comprise, for example, a processing circuit that is electrically coupled to at least one first electrode for sensing the near-field signals and at least one second electrode for sensing the far-field signals. As indicated herein and in the attached drawings, these electrodes may be located adjacent (e.g., on, next to, in between, etc.) an exterior surface of the housing. Based on the sensed signals, the processing circuit may monitor timing intervals between different cardiac events (e.g., between atrial events and ventricular events) to determine whether a patient has heart block. If heart block is indicated, the processing circuit may determine the degree of heart block and generate a corresponding indication of heart block. FIG. 12 illustrates sample operation that may be performed by circuitry of a LIMD or by some other suitable circuitry.

As represented by block 1202, near-field signals are sensed in a local cardiac chamber (e.g., the RA). These near-field signals originate from the local cardiac chamber and are detected, for example, via at least one first electrode of the LIMD.

As represented by block 1204, far-field signals are also sensed in the local cardiac chamber. These far-field signals originate from a cardiac chamber (e.g., the RV) that is adjacent the local cardiac chamber and are detected, for example, via at least one second electrode (e.g., one or more ring electrodes) of the LIMD.

As represented by block 1206, atrial events are identified based on the sensed near-field signals. As these events are collected over a period of time, a given one of these events may be an intrinsic event or a paced event (e.g., in cases where the patient has a pacemaker). Accordingly, for some cardiac beats, the operations of block 1206 involve identifying intrinsic atrial events that were detected as a result of the near-field signal sensing. Conversely, for other cardiac beats, the operations of block 1206 may involve identifying paced atrial events that were delivered upon failing to detect intrinsic atrial events as a result of the near-field signal sensing. Also, in a typical embodiment, an atrial refractory period (e.g., approximately 275-300 milliseconds) will be invoked upon detection of an atrial event to prevent detection of signals during that period.

As represented by block 1208, ventricular events are identified based on the sensed far-field signals. For example, the operations of block 1208 may involve, for each of the identified intrinsic and/or paced atrial events, determining based on the far-field signal sensing whether a ventricular event occurred within a defined timing window after the atrial event. Here, it should be appreciated that depending on the ability of the atrioventricular node to conduct the electrical activation between the atria and the ventricles, ventricular events may not be detected corresponding to every atrial activation.

The manner in which cardiac events are identified depends in some aspects on the electrode configuration employed for sensing cardiac activity. As discussed above, a LIMD may employ two, three, four, or more electrodes.

In some embodiments, a two-electrode model is employed. For example, to facilitate far-field sensing, an electrode spacing of approximately 1 centimeter may be employed. In this case, sensing via the two electrodes may detect both near-field signals and far-field signals (e.g., separated by an atrial-ventricular delay period).

In some embodiments, a three-electrode model is employed. Here, to facilitate near-field sensing, an electrode spacing of approximately 1 millimeter may be employed between a first electrode and a second electrode. To facilitate far-field sensing, an electrode spacing of approximately 1 centimeter may be employed between the second electrode and a third electrode. In this case, sensing via the first set of electrodes may primarily detect the near-field signals (e.g., the sensed far-field signals may be very small). In addition, sensing via the second set of electrodes may detect both the near field signals and the far-field signals (e.g., separated by an atrial-ventricular delay period).

As represented by block 1210, timing intervals based on the identified atrial and ventricular events are then determined. For example, in some embodiments, this operation involves generating a histogram based on the identified atrial and ventricular events, whereby the histogram indicates the timing intervals between corresponding pairs of atrial and ventricular events in cases where a ventricular event was detected. In the cases where ventricular events were not detected, the absence of these events will provide an indication of the patient's cardiac health.

As represented by block 1212, a cardiac diagnostic indication is generated based on the timing intervals. For example, a high percentage of atrial-to-ventricular event timing intervals in the range of 180 milliseconds for intrinsic atrial events or 120 milliseconds for paced atrial events may be considered indicative of appropriate function of the atrioventricular node. First-degree heart block may be detected when the ratio of atrial-to-ventricular events is unity but the timing between atrial and ventricular events is consistently prolonged.

In contrast, the presence of a higher percentage of other atrial-to-ventricular event timing intervals may be indicative of a degree of heart block. For example, third degree heart block may be indicated if the histogram indicates a broadening and/or a time shift of the range of timing intervals between atrial and ventricular events.

As another example, second-degree heart block may be indicated if the histogram indicates a reduction in the magnitude of the accumulated histogram values for the ventricular events. Here, the reduction in magnitude of the histogram is indicative of skipped ventricular events. For example, rather than a 1:1 correlation between atrial events and ventricular events, a 5:4 or some other non-unity correlation between atrial events and ventricular events is occurring. Variability of the range of timing intervals between atrial and ventricular events may be used to classify further the second-degree heart block as type A or B.

As yet another example, third-degree heart block may be indicated if the histogram indicates a flattening and widening of the accumulated histogram values for the ventricular events. Here, the flattening and widening of the histogram is indicative of a lack of synchronization between atrial events and ventricular events. For example, a correlation on the order of 2:1 or worse between atrial events and ventricular events may be indicative of third degree heart block.

The generation of the diagnostic indication may involve different types of operations in different embodiments. For example, in some embodiments, generating an indication involves storing an appropriate value in a memory device (e.g., a register, RAM, FLASH, etc.). In some embodiments, generating an indication involves sending a message (e.g., via radiofrequency signaling) that includes diagnostic information. Such a message may be sent to, for example, an external monitoring device (e.g., that will alert a patent and/or physician as to the patient's condition), another implantable device (e.g., a cardiac stimulation device), or some other device that takes action based on the indication.

Figure 13:
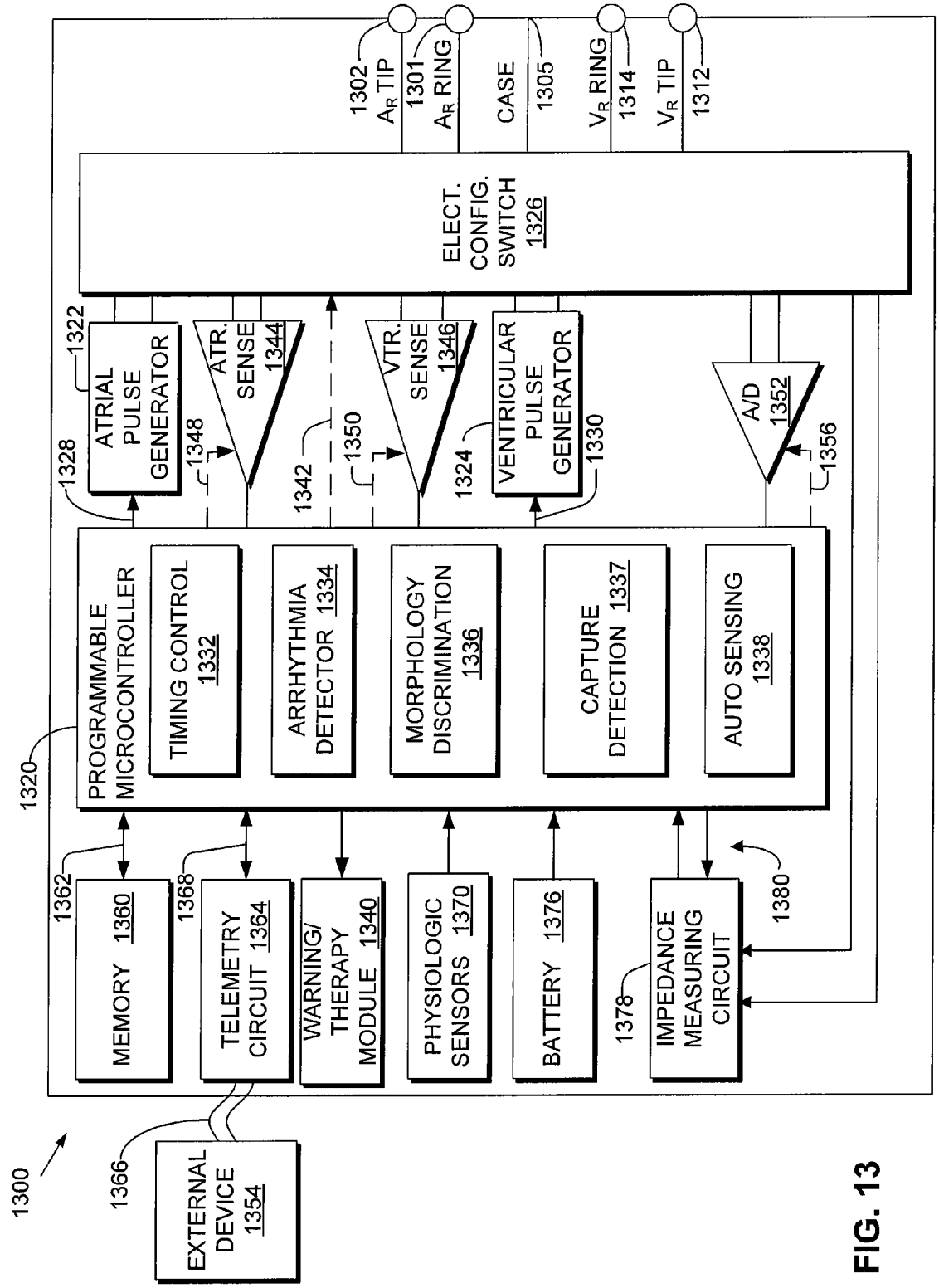
FIG. 13 is a simplified functional block diagram of an embodiment of a LIMD, illustrating basic elements that may be configured to sense conditions in the patient, deliver therapy to the patient, or provide some combination thereof.

FIG. 13 illustrates sample components of an embodiment of an implantable intra-cardiac medical device 1300 (e.g., a stimulation device such as an implantable cardioverter defibrillator, a pacemaker, etc., or a monitoring device) that may be configured in accordance with the various embodiments that are described herein. It is to be appreciated and understood that other cardiac devices can be used and that the description below is given, in its specific context, to assist the reader in understanding, with more clarity, the embodiments described herein.

In various embodiments, the device 1300 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

A housing 1305 for the device 1300 is often referred to as the "can", "case" or "case electrode", and may be programmably selected to act as the return electrode for all "unipolar" modes. The housing 1305 may further be used as a return electrode alone or in combination with one or more coil electrodes (not shown) for shocking purposes. As discussed herein, the housing 1305 may be constructed of a biocompatible material (e.g., titanium) to facilitate implant within a patient.

The device 1300 further includes a plurality of terminals that connect the internal circuitry of the device 1300 to electrodes 1301, 1302, 1312, and 1314 of the device 1300. Here, the name of the electrodes to which each terminal is connected is shown next to that terminal. The device 1300 may be configured to include various other terminals depending on the requirements of a given application.

To achieve right atrial sensing and pacing, a right atrial tip terminal ($A_R$ TIP) is adapted for connection to a right atrial tip electrode 1302. A right atrial ring terminal ($A_R$ RING) may also be included and adapted for connection to a right atrial ring electrode 1301. To achieve right ventricular sensing and pacing, a right ventricular tip terminal ($V_R$ TIP) and a right ventricular ring terminal ($V_R$ RING) are adapted for connection to a right ventricular tip electrode 1312 and a right ventricular ring electrode 1314, respectively.

At the core of the device 1300 is a programmable microcontroller 1320 that controls the various modes of stimulation therapy. As is well known in the art, microcontroller 1320 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 1320 includes the ability to process or monitor input signals (data or information) as controlled by a program code stored in a designated block of memory. The type of microcontroller is not critical to the described implementations. Rather, any suitable microcontroller 1320 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 13 also shows an atrial pulse generator 1322 and a ventricular pulse generator 1324 that generate pacing stimulation pulses for delivery by the right atrial electrodes, the right ventricular electrode, or some combination of these electrodes via an electrode configuration switch 1326. It is understood that in order to provide stimulation therapy in each of the four chambers of the heart, the atrial and ventricular pulse generators 1322 and 1324 may include dedicated, independent pulse generators, multiplexed pulse generators, or shared pulse generators. The pulse generators 1322 and 1324 are controlled by the microcontroller 1320 via appropriate control signals 1328 and 1330, respectively, to trigger or inhibit the stimulation pulses.

Microcontroller 1320 further includes timing control circuitry 1332 to control the timing of the stimulation pulses (e.g., pacing rate, atrioventricular (AV) delay, inter-atrial conduction (A-A) delay, or inter-ventricular conduction (V-V) delay, etc.) or other operations, as well as to keep track of the timing of refractory periods, blanking intervals, noise detection windows, evoked response windows, alert intervals, marker channel timing, etc., as known in the art.

Microcontroller 1320 further includes an arrhythmia detector 1334. The arrhythmia detector 1334 may be utilized by the device 1300 for determining desirable times to administer various therapies. The arrhythmia detector 1334 may be implemented, for example, in hardware as part of the microcontroller 1320, or as software/firmware instructions programmed into the device 1300 and executed on the microcontroller 1320 during certain modes of operation.

Microcontroller 1320 may include a morphology discrimination module 1336, a capture detection module 1337 and an auto sensing module 1338. These modules are optionally used to implement various exemplary recognition algorithms or methods. The aforementioned components may be implemented, for example, in hardware as part of the microcontroller 1320, or as software/firmware instructions programmed into the device 1300 and executed on the microcontroller 1320 during certain modes of operation.

The electrode configuration switch 1326 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 1326, in response to a control signal 1342 from the microcontroller 1320, may be used to determine the polarity of the stimulation pulses (e.g., unipolar, bipolar, combipolar, etc.) by selectively closing the appropriate combination of switches (not shown) as is known in the art.

Atrial sensing circuits 1344 and ventricular sensing circuits 1346 may also be selectively coupled to the right atrial electrodes and the right ventricular electrodes through the switch 1326 for detecting the presence of cardiac activity in each of the four chambers of the heart. Accordingly, the atrial and ventricular sensing circuits 1344 and 1346 may include dedicated sense amplifiers, multiplexed amplifiers, or shared amplifiers. Switch 1326 determines the "sensing polarity" of the cardiac signal by selectively closing the appropriate switches, as is also known in the art. In this way, the clinician may program the sensing polarity independent of the stimulation polarity. The sensing circuits (e.g., circuits 1344 and 1346) are optionally capable of obtaining information indicative of tissue capture.

Each sensing circuit 1344 and 1346 preferably employs one or more low power, precision amplifiers with programmable gain, automatic gain control, bandpass filtering, a threshold detection circuit, or some combination of these components, to selectively sense the cardiac signal of interest. The automatic gain control enables the device 1300 to deal effectively with the difficult problem of sensing the low amplitude signal characteristics of atrial or ventricular fibrillation.

The outputs of the atrial and ventricular sensing circuits 1344 and 1346 are connected to the microcontroller 1320, which, in turn, is able to trigger or inhibit the atrial and ventricular pulse generators 1322 and 1324, respectively, in a demand fashion in response to the absence or presence of cardiac activity in the appropriate chambers of the heart. Furthermore, as described herein, the microcontroller 1320 is also capable of analyzing information output from the sensing circuits 1344 and 1346, a data acquisition system 1352, or both. This information may be used to determine or detect whether and to what degree tissue capture has occurred and to program a pulse, or pulses, in response to such determinations. The sensing circuits 1344 and 1346, in turn, receive control signals over signal lines 1348 and 1350, respectively, from the microcontroller 1320 for purposes of controlling the gain, threshold, polarization charge removal circuitry (not shown), and the timing of any blocking circuitry (not shown) coupled to the inputs of the sensing circuits 1344 and 1346 as is known in the art.

For arrhythmia detection, the device 1300 utilizes the atrial and ventricular sensing circuits 1344 and 1346 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 1334 of the microcontroller 1320 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 1352. The data acquisition system 1352 is configured (e.g., via signal line 1356) to acquire intra-cardiac electrogram ("IEGM") signals or other signals, convert the raw analog data into a digital signal, and store the digital signals for later processing, for telemetric transmission to an external device 1354, or both. For example, the data acquisition system 1352 may be coupled to the right atrial electrodes and the right ventricular electrodes through the switch 1326 to sample cardiac signals across any pair of desired electrodes.

The data acquisition system 1352 also may be coupled to receive signals from other input devices. For example, the data acquisition system 1352 may sample signals from a physiologic sensor 1370 or other components shown in FIG. 13 (connections not shown).

The microcontroller 1320 is further coupled to a memory 1360 by a suitable data/address bus 1362, wherein the programmable operating parameters used by the microcontroller 1320 are stored and modified, as required, in order to customize the operation of the device 1300 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 1352), which data may then be used for subsequent analysis to guide the programming of the device 1300.

Advantageously, the operating parameters of the implantable device 1300 may be non-invasively programmed into the memory 1360 through a telemetry circuit 1364 in telemetric communication via communication link 1366 with the external device 1354, such as a programmer, transtelephonic transceiver, a diagnostic system analyzer or some other device. The microcontroller 1320 activates the telemetry circuit 1364 with a control signal (e.g., via bus 1368). The telemetry circuit 1364 advantageously allows intra-cardiac electrograms and status information relating to the operation of the device 1300 (as contained in the microcontroller 1320 or memory 1360) to be sent to the external device 1354 through an established communication link 1366.

The device 1300 can further include one or more physiologic sensors 1370. In some embodiments the device 1300 may include a "rate-responsive" sensor that may provide, for example, information to aid in adjustment of pacing stimulation rate according to the exercise state of the patient. One or more physiologic sensors 1370 (e.g., a pressure sensor) may further be used to detect changes in cardiac output, changes in the physiological condition of the heart, or diurnal changes in activity (e.g., detecting sleep and wake states). Accordingly, the microcontroller 1320 responds by adjusting the various pacing parameters (such as rate, A-V Delay, V-V Delay, etc.) at which the atrial and ventricular pulse generators 1322 and 1324 generate stimulation pulses.

While shown as being included within the device 1300, it is to be understood that a physiologic sensor 1370 may also be external to the device 1300, yet still be implanted within or carried by the patient. Examples of physiologic sensors that may be implemented in conjunction with the device 1300 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 1370 may optionally include one or more of components to help detect movement (via, e.g., a position sensor or an accelerometer) and minute ventilation (via an MV sensor) in the patient. Signals generated by the position sensor and MV sensor may be passed to the microcontroller 1320 for analysis in determining whether to adjust the pacing rate, etc. The microcontroller 1320 may thus monitor the signals for indications of the patient's position and activity status, such as whether the patient is climbing up stairs or descending down stairs or whether the patient is sitting up after lying down.

The device 1300 additionally includes a battery 1376 that provides operating power to all of the circuits shown in FIG. 13. For a device 1300 which employs shocking therapy, the battery 1376 is capable of operating at low current drains (e.g., preferably less than 10 μA) for long periods of time, and is capable of providing high-current pulses (for capacitor charging) when the patient requires a shock pulse (e.g., preferably, in excess of 2 A, at voltages above 200 V, for periods of 10 seconds or more). The battery 1376 also desirably has a predictable discharge characteristic so that elective replacement time can be detected. Accordingly, the device 1300 preferably employs lithium or other suitable battery technology.

The device 1300 can further include magnet detection circuitry (not shown), coupled to the microcontroller 1320, to detect when a magnet is placed over the device 1300. A magnet may be used by a clinician to perform various test functions of the device 1300 and to signal the microcontroller 1320 that the external device 1354 is in place to receive data from or transmit data to the microcontroller 1320 through the telemetry circuit 1364.

The device 1300 further includes an impedance measuring circuit 1378 that is enabled by the microcontroller 1320 via a control signal 1380. The known uses for an impedance measuring circuit 1378 include, but are not limited to, electrode impedance surveillance during the acute and chronic phases for proper performance, electrode positioning or dislodgement; detecting operable electrodes and automatically switching to an operable pair if dislodgement occurs; measuring respiration or minute ventilation; measuring thoracic impedance for determining shock thresholds; detecting when the device 1300 has been implanted; measuring stroke volume; and detecting the opening of heart valves, etc. The impedance measuring circuit 1378 is advantageously coupled to the switch 1326 so that any desired electrode may be used.

In the case where the device 1300 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 1320 may include a shocking circuit (not shown). The shocking circuit generates shocking pulses of low (e.g., up to 0.5 J), moderate (e.g., 0.5 J to 10 J), or high energy (e.g., 11 J to 40 J), as controlled by the microcontroller 1320. Such shocking pulses may be applied to the patient's heart H through, for example, two or more shocking electrodes (not shown).

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 1320 is capable of controlling the synchronous or asynchronous delivery of the shocking pulses.

The device 1300 thus illustrates several components that may provide the intra-cardiac medical device functionality described above in conjunction with FIGS. 1-11. For example, the microcontroller 1320 (e.g., a processor providing signal processing functionality) may implement or support at least a portion of the processing functionality discussed above. Also, one or more of the switch 1326, the sense circuits 1344, 1346, and the data acquisition system 1352 may acquire cardiac signals that are used in the signal acquisition operations discussed above. Similarly, one or more of the switch 1326 and the pulse generator circuits 1322, 1324 may be used to provide stimulation signals that are used in the cardiac stimulation operations discussed above. The data described above (e.g., morphology templates) may be stored in the data memory 1360. The physiologic sensors 1370 may comprise the electro-magnetic sensor(s) discussed above. Thus, in general, the processing circuitry described herein (e.g., the processing circuit 110 or 1106) may correspond to one or more of the illustrated components of the device 1300.

It should be appreciated that various modifications may be incorporated into the disclosed embodiments based on the teachings herein. For example, the structure and functionality taught herein may be incorporated into types of devices other than the specific types of devices described above. In addition, electrodes for a LIMD may be implemented in different ways in different embodiments based on the teachings herein. Different types of structural members and mechanical support structures may be employed in conjunction with a LIMD as taught herein. Also, various algorithms or techniques may be employed to identify events in various cardiac chambers (e.g., RA, RV, LA, and LV chambers) in accordance with the teachings herein.

It should be appreciated from the above that the various structures and functions described herein may be incorporated into a variety of apparatuses (e.g., a stimulation device, a monitoring device, etc.) and implemented in a variety of ways. Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings (e.g., in the form of electrical conductors) represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements." For example, this terminology may include A, or B, or C, or A and B, or A and C, or A and B and C, or 2A, or 2B, or 2C, and so on.

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure.

What is claimed is:

1. A leadless intra-cardiac medical device, comprising:
a housing configured to be positioned entirely within an intra-cardiac space;
at least one first electrode located at a distal section of the housing;
at least one second electrode; and
a processing circuit located within an interior space of the housing and electrically coupled to the at least one first electrode and the at least one second electrode, wherein the processing circuit is configured to:
determine whether at least one ventricular event occurred based on near-field signals sensed using the at least one first electrode,
determine whether at least one atrial event occurred based on far-field signals sensed using the at least one second electrode; and
generate at least one cardiac stimulation pulse based on the determination of whether the at least one ventricular event occurred and the determination of whether the at least one atrial event occurred.

2. The device of claim 1, wherein:
the determination of whether the at least one ventricular event occurred comprises identifying timing of an R wave; and
the determination of whether the at least one atrial event occurred comprises identifying timing of a P wave based on the identified timing of the R wave.

3. The device of claim 1, wherein the determination of whether the at least one atrial event occurred comprises:
filtering the far-field signals based on a first bandwidth;
filtering the far-field signals based on a second bandwidth, wherein the first bandwidth is narrower than the second bandwidth; and
comparing the filtered far-field signals to identify a P wave.

4. The device of claim 1, wherein:
the determination of whether the at least one ventricular event occurred comprises correlating a morphology derived from the near-field signals with at least one ventricular morphology template; and
the determination of whether the at least one atrial event occurred comprises correlating a morphology derived from the far-field signals with at least one atrial morphology template.

5. The device of claim 1, further comprising at least one electro-mechanical sensor, wherein
the processing circuit is further configured to receive signals from the at least one electro-mechanical sensor;
the determination of whether the at least one ventricular event occurred is further based on a first portion of the signals received from the at least one electro-mechanical sensor; and the determination of whether the at least one atrial event occurred is further based on a second portion of the signals received from the at least one electro-mechanical sensor.

6. The device of claim 1, wherein:
the at least one first electrode comprises at least one helix electrode; and
the at least one second electrode comprises at least one first ring electrode.

7. The device of claim 6, wherein:
the at least one first electrode further comprises at least one second ring electrode; and
the at least one first ring electrode comprises a plurality of ring electrodes.

8. The device of claim 1, wherein:
the at least one first electrode comprises a first bipolar electrode pair; and
the at least one second electrode comprises a second bipolar electrode pair.

9. The device of claim 1, wherein the housing has a cross-sectional width of less than 6 millimeters.

10. The device of claim 9, wherein the housing has a length of at least 30 millimeters.

11. The device of claim 9, wherein the housing has a length of at least 60 millimeters.

12. The device of claim 1, wherein a surface area of each electrode of the at least one second electrode is greater than 2 square millimeters.

13. The device of claim 1, wherein:
the at least one second electrode comprises a pair of electrodes; and
a distance between the pair of electrodes is at least 15 millimeters.

14. The device of claim 1, wherein:
the at least one second electrode comprises a pair of electrodes; and
at least a portion of an exterior surface of the housing between the pair of electrodes is covered by an electrical insulator.

15. The device of claim 1, further comprising a plurality of insulators for electrically insulating the housing from the at least one first electrode and the at least one second electrode.

16. The device of claim 1, wherein the at least one second electrode is located at a proximal section of the housing.

17. The device of claim 16, wherein the proximal section of the housing has a cross-sectional dimension that is smaller than a cross-sectional dimension of the distal section of the housing.

18. The device of claim 16, wherein:
the housing has a length that is greater than 60 millimeters;
the housing comprises a middle section between the proximal section and the distal section;
the middle section of the housing has a cross-sectional dimension that is smaller than a cross-sectional dimension of the distal section of the housing; and
the cross-sectional dimension of the middle section of the housing is smaller than a cross-sectional dimension of the proximal section of the housing.

19. The device of claim 1, further comprising an elongated structural member that extends from the proximal section of the housing, wherein the elongated structural member comprises the at least one second electrode.

20. The device of claim 19, wherein the elongated structural member has a length of at least 30 millimeters.

21. The device of claim 1, further comprising an elongated mechanical support structure that extends from the proximal section of the housing, wherein the elongated mechanical support structure comprises the at least one second electrode.

22. A leadless intra-cardiac medical device that does not employ electrodes for cardiac sensing, comprising:
a housing adapted to be positioned entirely within an intra-cardiac space;
at least one electro-mechanical sensor located within an interior space of the housing; and
a processing circuit located within the interior space of the housing and electrically coupled to the at least one electro-mechanical sensor, wherein the processing circuit is configured to:
determine, based on signals received from the at least one electro-mechanical sensor, whether at least one ventricular event occurred and whether at least one atrial event occurred; and
generate at least one cardiac stimulation pulse based on the determination of whether the at least one ventricular event occurred and whether the at least one atrial event occurred.

23. The device of claim 22, wherein:
the determination of whether the at least one ventricular event occurred comprises correlating mechanical activity information derived from a first portion of the signals received from the at least one electro-mechanical sensor with a ventricular mechanical activity template; and
the determination of whether the at least one atrial event occurred comprises correlating mechanical activity information derived from a second portion of the signals received from the at least one electro-mechanical sensor with an atrial mechanical activity template.

24. The device of claim 22, wherein:
the determination of whether the at least one ventricular event occurred comprises identifying timing of an R wave; and
the determination of whether the at least one atrial event occurred comprises identifying timing of a P wave based on the identified timing of the R wave.

25. The device of claim 22, wherein the at least one electro-mechanical sensor comprises a plurality of accelerometers configured to measure acceleration in different directions.

26. A leadless intra-cardiac medical device, comprising:
a housing configured to be positioned entirely within an intra-cardiac space;
at least one first electrode located adjacent an exterior surface of the housing;
at least one second electrode located adjacent the exterior surface of the housing; and
a processing circuit located within an interior space of the housing and electrically coupled to the at least one first electrode and the at least one second electrode, wherein the processing circuit is configured to:
sense near-field signals in an atrium using the at least one first electrode;
sense far-field signals in the atrium using the at least one second electrode;
identify atrial events based on the sensed near-field signals;
identify ventricular events based on the sensed far-field signals;
determine timing intervals based on the identified atrial events and the identified ventricular events; and
generate a cardiac diagnostic indication based on the timing intervals.

27. The device of claim 26, wherein the determination of the timing intervals comprises generating a histogram based on the identified atrial events and the identified ventricular events.

28. The device of claim 26, wherein:
the identification of the atrial events comprises: identifying intrinsic atrial events that were detected as a result of the near-field signal sensing and/or identifying paced atrial events that were delivered upon failing to detect intrinsic atrial events as a result of the near-field signal sensing; and
the identification of the ventricular events comprises, for each of the identified intrinsic and/or paced atrial events, determining based on the far-field signal sensing whether a ventricular event occurred within a defined timing window after the atrial event.

29. The device of claim 28, wherein the generation of the cardiac diagnostic indication comprises determining a degree of heart block based on the timing intervals and generating an indication of the degree of heart block.

30. The device of claim 26, wherein:
the at least one second electrode comprises a pair of electrodes; and
a distance between the pair of electrodes is at least 15 millimeters.

31. The device of claim 26, wherein:
the at least one second electrode comprises a pair of electrodes; and
at least a portion of an exterior surface of the housing between the pair of electrodes is covered by an electrical insulator.

32. A cardiac diagnostic method, comprising:
sensing near-field signals in an atrium using at least one first electrode of a leadless intra-cardiac medical device configured to be positioned entirely within an intra-cardiac space;
sensing far-field signals in the atrium using at least one second electrode of a leadless intra-cardiac medical device configured to positioned entirely within an intra-cardiac space;
identifying atrial cardiac events based on the sensed near-field signals;
identifying ventricular events based on the sensed far-field signals;
determining timing intervals based on the identified atrial events and the identified ventricular events; and
generating a cardiac diagnostic indication based on the timing intervals.

33. The method of claim 32, wherein the leadless intra-cardiac medical device is implanted in a heart such that no part of the leadless intra-cardiac medical device is located in a cardiac chamber from which the far-field signals originate.

* * * * *